(12) United States Patent
Merchant et al.

(10) Patent No.: US 10,041,956 B2
(45) Date of Patent: Aug. 7, 2018

(54) METHODS AND KITS FOR PREDICTING A RESPONSE TO AN ERYTHROPOIETIC AGENT

(71) Applicant: University of Louisville Research Foundation, Inc., Louisville, KY (US)

(72) Inventors: Michael L. Merchant, Louisville, KY (US); Jon B. Klein, Louisville, KY (US); Michael E. Brier, Sellersburg, IN (US); Adam E. Gaweda, Jeffersonville, IN (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 239 days.

(21) Appl. No.: 14/712,323

(22) Filed: May 14, 2015

(65) Prior Publication Data

US 2015/0247868 A1 Sep. 3, 2015

Related U.S. Application Data

(63) Continuation of application No. 13/167,478, filed on Jun. 23, 2011, now Pat. No. 9,057,731.

(60) Provisional application No. 61/357,843, filed on Jun. 23, 2010.

(51) Int. Cl.
*G01N 33/68* (2006.01)

(52) U.S. Cl.
CPC ......... *G01N 33/6893* (2013.01); *G01N 33/68* (2013.01); *G01N 33/6863* (2013.01); *G01N 2333/47* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,056,734 A | 5/2000 | Jacobsen et al. |
| 6,267,116 B1 | 7/2001 | McMichael |
| 6,575,169 B2 | 6/2003 | McMichael |
| 6,658,396 B1 | 12/2003 | Tang et al. |
| 6,747,002 B2 | 6/2004 | Cheung et al. |
| 6,822,554 B2 | 11/2004 | Vrijens et al. |
| 6,883,521 B2 | 4/2005 | McMichael |
| 7,232,797 B2 | 6/2007 | Farrell |
| 7,651,845 B2 | 1/2010 | Doyle et al. |

FOREIGN PATENT DOCUMENTS

| | | | |
|---|---|---|---|
| WO | 2007022248 A2 | 2/2007 | |
| WO | WO-2011025572 A1 * | 3/2011 | ......... A61K 39/0011 |

OTHER PUBLICATIONS

Villanueva et al. "Differential exoprotease activities confer tumor-specific serum peptidome patterns", J. Clin. Invest. 116:271-284 (2006), including accompanying online Supplemental Material retrieved from http://www.jci.org/articles/view/26022/sd/1 (48 pages total).*
Andrews, N.C., "Anemia of inflammation: the cytokine-hepcidin link", J. Clin. Invest., 2004, vol. 113, pp. 1251-1253.
Bawumia et al., "Specificity of interactions of galectin-3 with Chrp a cysteine- and histidine-rich cytoplasmic protein", Biochimie, 2005, vol. 85, pp. 189-194.
Blanchard et al., "Oncostatin M regulates the synthesis and turnover of gp130, leukemia inhibitory factor receptor α, and oncostatin M receptor β by distinct mechanisms", J. Biol. Chem., 2001, vol. 50, pp. 47038-47045.
Borawski et al., "Inflammatory markers and platelet aggregation tests as predictors of hemoglobin and endogenous erythropoietin levels in hemodialysis patients", Nephron, 2002, vol. 91, pp. 671-681.
Brown et al., "Purification and characterization of cytostatic lymphokines produced by activated human T lymphocytes: synergistic antoproliferative activity of transforming growth factor beta 1, interferon-gamma, and oncostatin M for human melanoma cells", J. Immunol., 1987, vol. 139, pp. 2977-2983.
Chen et al., "Expression of short-form oncostatin M receptor as a decoy receptor in lung adenocarcinomas", J Pathol, 2008, vol. 215, pp. 290-299.
Danielson, B., "R-HuEPO hyporesponsiveness—who and why?" Nephrol. Dial. Transplant, 1995, vol. 10, pp. 69-73.
Gaweda et al., "Model Predictive Control of Erythropoietin Administration in the Anemia of ESRD", American Journal of Kidney Diseases, 2008, vol. 51(1), pp. 71-79.
Goicoechea et al., "Role of cytokines in the response to erythropoietin in hemodialysis patients", Kidney Int., 1998, vol. 54, pp. 1337-1343.
Inrig et al., "Association between high-dose ESA, inflammatory biomarkers, and soluble erythropoietin receptors", J. Am. Soc. Nephrol., 2009, vol. 20, p. 143A.
Kaysen, GA, "The microinflammatory state in uremia: causes and potential consequences", J. Am. Soc. Nephrol., 2001, vol. 12, pp. 1549-1557.
Khankin et al., "Soluble erythropoietin receptor contributes to erythropoietin resistance in end-stage renal disease", PLoS One, 2010, vol. 16, p. e9246.
Malik et al., "Molecular cloning, sequence analysis, and functional expression of a novel growth regulator, oncostatin", M. Mol. Cell Biol, 1989, vol. 9, pp. 2847-2853.
Mann et al., "Precision proteomics: The case for high resolution and high mass accuracy", Proc. Nat. Acad. Sci., 2008, vol. 105, pp. 18132-18138.
Matthews et al., "Cellular cholesterol depletion triggers shedding of the human interleukin-6 receptor by ADAM10 and ADAM17 (TACE)", J Biol Chem, 2003, vol. 278, pp. 38829-38839.

(Continued)

*Primary Examiner* — Christine Foster
(74) *Attorney, Agent, or Firm* — Stites & Harbison, PLLC; Terry L. Wright

(57) ABSTRACT

Methods for predicting a response to an erythropoietic agent in a subject include providing a biological sample from the subject, and determining an amount in the sample of at least one peptide selected from the group consisting of SEQ ID NOS: 1-17. If there is a measurable difference in the amount of the at least one peptide in the sample, when compared to a control level of the same peptide, the subject is then predicted to have a good response or a poor response to the erythropoietic agent.

13 Claims, 5 Drawing Sheets

(56) References Cited

OTHER PUBLICATIONS

Menon et al., "Signals for stress erythropoiesis are integrated via and erythropoietin receptor-phosphotyrosine-343-Stat5 axis", J. Clin. Invest, 2006, vol. 116, pp. 683-694.

Menon et al., "Interaction of a novel cysteine and histidine-rich cytoplasmic protein with galectin-3 in a carbohydrate-independent17 manner", FEBS Lett., 2000, vol. 470, pp. 227-231.

Merchant et al., "Urinary peptidome may predict renal function decline in type 1 diabetes and microalbuminuria", J Am Sac Nephrol, 2009, vol. 20, pp. 2065-2074.

Merchant et al., "Proteomic analysis of renal calculi indicates an important role for inflammatory processes in calcium stone formation", Am J Physiol Renal Physiol, 2008, vol. 295, pp. F1254-1258.

Mosley et al., "Dual oncostatin M (OSM) receptors. Cloning and characterization of an alternative signaling subunit conferring OSM-specific receptor activation", J Biol Chem, 1996, vol. 271, pp. 32635-32643.

Narayanan, S., "Multifunctional roles of thrombin", Ann. Clin. Lab. Sci., 1999, vol. 29, pp. 275-280.

Nemeth et al., "IL-6 mediates hypoferremia of inflammation by inducing the synthesis of the iron regulatory hormone hepcidin", J. Clin. Invest, 2004, vol. 113, pp. 1271-1276.

Tanaka et al., "Targeted disruption of oncostatin M receptor results in altered hematopoiesis", Blood, 2003, vol. 102, pp. 3154-3162.

Thoma et al., "Oncostatin M and leukemia inhibitory factor trigger overlapping and different signals through partially shared receptor complexes", J Biol Chem, 1994, vol. 269, pp. 6215-6222.

Van Der Putteen et al., "Mechanisms of disease: erythropoietin resistance in patients with both heart and kidney failure", Nat. Clin. Pract. Nephrol., 2008, vol. 4, pp. 47-57.

Vollner et al., "Hypoxia-inducible factor 1α is up-regulated by oncostatin M and participates in oncostatin M signaling", Hepatology, 2009, vol. 50, pp. 253-260.

Szczech et al., "Secondary analysis of the CHOIR trial epoetin-α dose and achieved hemoglobin outcomes", Kidney Int, 2008, vol. 74, pp. 791-798.

Zhang et al., "Epoetin requirement predict mortality in hemodialysis patients", Am. J. Kidney Dis, 2004, vol. 44, pp. 866-876.

Cornes et al., "Erythropoietic therapy for the treatment of anemia in patients with cancer: a valuable clinical and economic option," Current Medical Research and Opinion, 2007, vol. 23, pp. 357-368.

\* cited by examiner

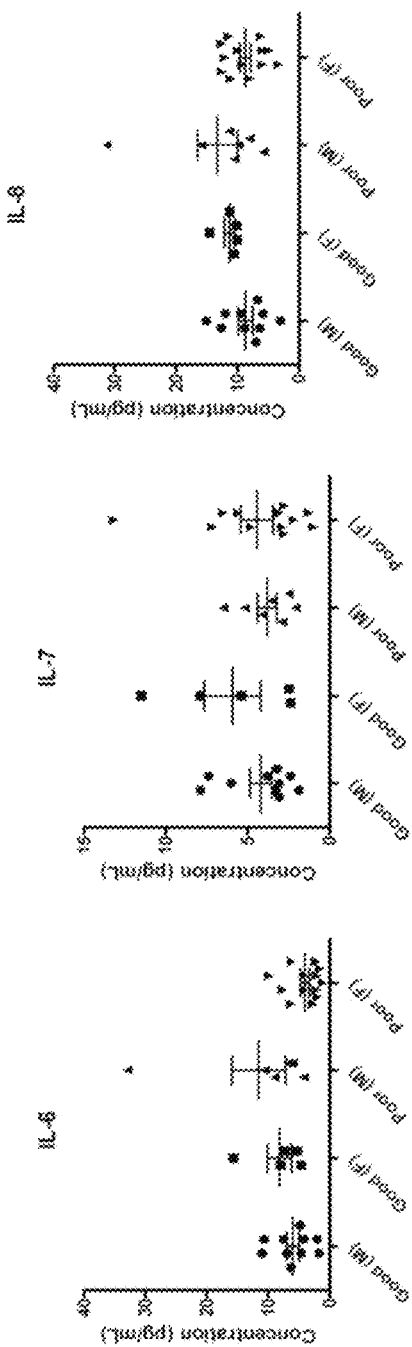
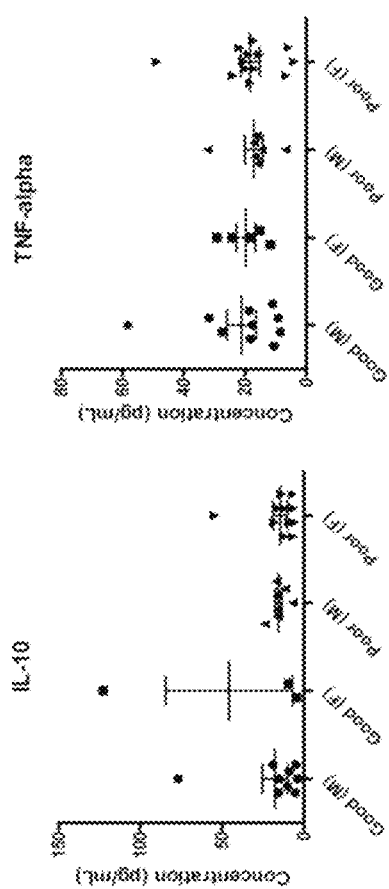
FIG. 2A  FIG. 2B  FIG. 2C  FIG. 2D  FIG. 2E

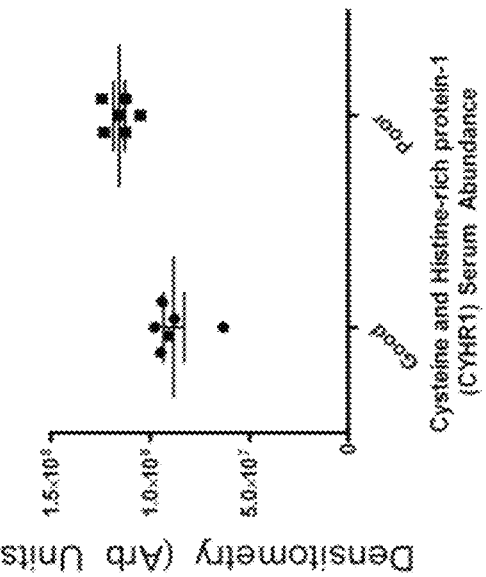
FIG. 5A
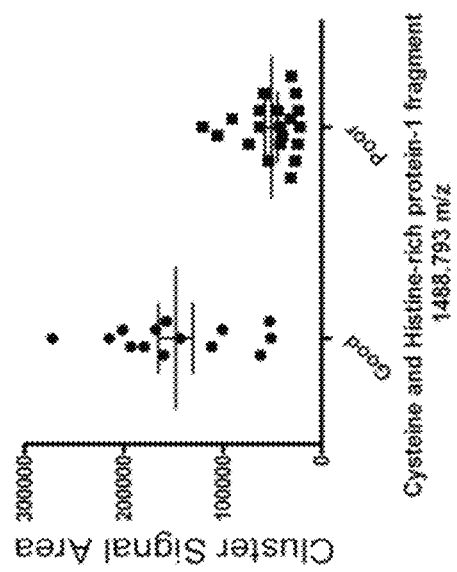
FIG. 5B
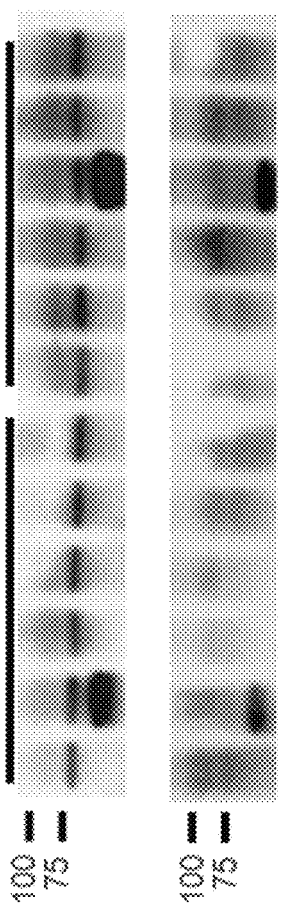
FIG. 5C
FIG. 5D

SEQUENCE LISTING

```
<160> NUMBER OF SEQ ID NOS: 34

<210> SEQ ID NO 1
<211> LENGTH: 13
<212> TYPE: PRT
<213> ORGANISM: Homo sapiens

<400> SEQUENCE: 1

Ser Gly Glu Gly Asp Phe Leu Ala Glu Gly Gly Gly Val
1               5                   10

<210> SEQ ID NO 2
<211> LENGTH: 13
<212> TYPE: PRT
<213> ORGANISM: Homo sapiens

<400> SEQUENCE: 2

Gly Glu Gly Asp Phe Leu Ala Glu Gly Gly Gly Val Arg
1               5                   10

<210> SEQ ID NO 3
<211> LENGTH: 15
<212> TYPE: PRT
<213> ORGANISM: Homo sapiens

<400> SEQUENCE: 3

Asp Ser Gly Glu Gly Asp Phe Leu Ala Glu Gly Gly Gly Val Arg
1               5                   10                  15

<210> SEQ ID NO 4
```

```
<211> LENGTH: 15
<212> TYPE: PRT
<213> ORGANISM: Homo sapiens
<220> FEATURE:
<221> NAME/KEY: Hydroxyl Group
<222> LOCATION: (7)..(7)
<223> OTHER INFORMATION: Hydroxyl Group

<400> SEQUENCE: 4

Asp Ser Gly Glu Gly Asp Phe Leu Ala Glu Gly Gly Gly Val Arg
1               5                   10                  15

<210> SEQ ID NO 5
<211> LENGTH: 16
<212> TYPE: PRT
<213> ORGANISM: Homo sapiens

<400> SEQUENCE: 5

Ala Asp Ser Gly Glu Gly Asp Phe Leu Ala Glu Gly Gly Gly Val Arg
1               5                   10                  15

<210> SEQ ID NO 6
<211> LENGTH: 14
<212> TYPE: PRT
<213> ORGANISM: Homo sapiens

<400> SEQUENCE: 6

Ser Gly Glu Gly Asp Phe Leu Ala Glu Gly Gly Gly Val Arg
1               5                   10

<210> SEQ ID NO 7
<211> LENGTH: 22
<212> TYPE: PRT
<213> ORGANISM: Homo sapiens

<400> SEQUENCE: 7

Ser Ser Tyr Ser Lys Gln Phe Thr Ser Ser Thr Ser Tyr Asn Arg Gly
1               5                   10                  15

Asp Ser Thr Phe Glu Ser
            20

<210> SEQ ID NO 8
<211> LENGTH: 23
<212> TYPE: PRT
<213> ORGANISM: Homo sapiens

<400> SEQUENCE: 8

Ser Ser Ser Tyr Ser Lys Gln Phe Thr Ser Ser Thr Ser Tyr Asn Arg
1               5                   10                  15

Gly Asp Ser Thr Phe Glu Ser
            20

<210> SEQ ID NO 9
<211> LENGTH: 25
<212> TYPE: PRT
<213> ORGANISM: Homo sapiens

<400> SEQUENCE: 9

Ser Ser Ser Tyr Ser Lys Gln Phe Thr Ser Ser Thr Ser Tyr Asn Arg
1               5                   10                  15

Gly Asp Ser Thr Phe Glu Ser Lys Ser
            20                  25

<210> SEQ ID NO 10
```

```
<211> LENGTH: 26
<212> TYPE: PRT
<213> ORGANISM: Homo sapiens

<400> SEQUENCE: 10

Ser Ser Ser Tyr Ser Lys Gln Phe Thr Ser Ser Thr Ser Tyr Asn Arg
1               5                   10                  15

Gly Asp Ser Thr Phe Glu Ser Lys Ser Tyr
            20                  25

<210> SEQ ID NO 11
<211> LENGTH: 14
<212> TYPE: PRT
<213> ORGANISM: Homo sapiens
<220> FEATURE:
<221> NAME/KEY: Pyroglutamic acid derivative
<222> LOCATION: (1)..(1)
<223> OTHER INFORMATION: Pyroglutamic acid derivative

<400> SEQUENCE: 11

Gln Gly Val Asn Asp Asn Glu Glu Gly Phe Phe Ser Ala Arg
1               5                   10

<210> SEQ ID NO 12
<211> LENGTH: 11
<212> TYPE: PRT
<213> ORGANISM: Homo sapiens
<220> FEATURE:
<221> NAME/KEY: Acetyl group
<222> LOCATION: (1)..(1)
<223> OTHER INFORMATION: Acetyl group

<400> SEQUENCE: 12

Ser Glu Thr Ser Arg Thr Ala Phe Gly Gly Arg
1               5                   10

<210> SEQ ID NO 13
<211> LENGTH: 15
<212> TYPE: PRT
<213> ORGANISM: Homo sapiens

<400> SEQUENCE: 13

Ser His Leu Val Leu Gly Val Val Ser Leu His Ala Ala Val Ser
1               5                   10                  15

<210> SEQ ID NO 14
<211> LENGTH: 13
<212> TYPE: PRT
<213> ORGANISM: Homo sapiens

<400> SEQUENCE: 14

Ser Pro Met Tyr Ser Ile Ile Thr Pro Asn Ile Leu Arg
1               5                   10

<210> SEQ ID NO 15
<211> LENGTH: 11
<212> TYPE: PRT
<213> ORGANISM: Homo sapiens

<400> SEQUENCE: 15

Asn Lys Glu Val Glu Glu Glu Arg Ile Ala Gly
1               5                   10

<210> SEQ ID NO 16
<211> LENGTH: 13
<212> TYPE: PRT
```

-continued

<213> ORGANISM: Homo sapiens

<400> SEQUENCE: 16

Asn Lys Glu Val Glu Glu Glu Arg Ile Ala Gly Thr Glu
1               5                   10

<210> SEQ ID NO 17
<211> LENGTH: 13
<212> TYPE: PRT
<213> ORGANISM: Homo sapiens
<220> FEATURE:
<221> NAME/KEY: O-glucosamine modification
<222> LOCATION: (12)..(12)
<223> OTHER INFORMATION: O-glucosamine modification

<400> SEQUENCE: 17

Asn Lys Glu Val Glu Glu Glu Arg Ile Ala Gly Thr Glu
1               5                   10

<210> SEQ ID NO 18
<211> LENGTH: 15
<212> TYPE: PRT
<213> ORGANISM: Homo sapiens

<400> SEQUENCE: 18

Asp Ser Gly Glu Gly Asp Phe Leu Ala Glu Gly Gly Gly Val Arg
1               5                   10                  15

<210> SEQ ID NO 19
<211> LENGTH: 15
<212> TYPE: PRT
<213> ORGANISM: Homo sapiens

<400> SEQUENCE: 19

Ser Gly Glu Gly Asp Phe Leu Ala Glu Gly Gly Gly Val Arg Gly
1               5                   10                  15

<210> SEQ ID NO 20
<211> LENGTH: 17
<212> TYPE: PRT
<213> ORGANISM: Homo sapiens

<400> SEQUENCE: 20

Ala Asp Ser Gly Glu Gly Asp Phe Leu Ala Glu Gly Gly Gly Val Arg
1               5                   10                  15

Gly

<210> SEQ ID NO 21
<211> LENGTH: 17
<212> TYPE: PRT
<213> ORGANISM: Homo sapiens

<400> SEQUENCE: 21

Ala Asp Ser Gly Glu Gly Asp Phe Leu Ala Glu Gly Gly Gly Val Arg
1               5                   10                  15

Gly

<210> SEQ ID NO 22
<211> LENGTH: 18
<212> TYPE: PRT
<213> ORGANISM: Homo sapiens

<400> SEQUENCE: 22

Asp Ala Asp Ser Gly Glu Gly Asp Phe Leu Ala Glu Gly Gly Gly Val

```
1               5                   10                  15

Arg Gly

<210> SEQ ID NO 23
<211> LENGTH: 16
<212> TYPE: PRT
<213> ORGANISM: Homo sapiens

<400> SEQUENCE: 23

Asp Ser Gly Glu Gly Asp Phe Leu Ala Glu Gly Gly Val Arg Gly
1               5                   10                  15

<210> SEQ ID NO 24
<211> LENGTH: 24
<212> TYPE: PRT
<213> ORGANISM: Homo sapiens

<400> SEQUENCE: 24

Ser Ser Ser Tyr Ser Lys Gln Phe Thr Ser Ser Thr Ser Tyr Asn Arg
1               5                   10                  15

Gly Asp Ser Thr Phe Glu Ser Lys
            20

<210> SEQ ID NO 25
<211> LENGTH: 25
<212> TYPE: PRT
<213> ORGANISM: Homo sapiens

<400> SEQUENCE: 25

Lys Ser Ser Ser Tyr Ser Lys Gln Phe Thr Ser Ser Thr Ser Tyr Asn
1               5                   10                  15

Arg Gly Asp Ser Thr Phe Glu Ser Lys
            20                  25

<210> SEQ ID NO 26
<211> LENGTH: 27
<212> TYPE: PRT
<213> ORGANISM: Homo sapiens

<400> SEQUENCE: 26

Lys Ser Ser Ser Tyr Ser Lys Gln Phe Thr Ser Ser Thr Ser Tyr Asn
1               5                   10                  15

Arg Gly Asp Ser Thr Phe Glu Ser Lys Ser Tyr
            20                  25

<210> SEQ ID NO 27
<211> LENGTH: 28
<212> TYPE: PRT
<213> ORGANISM: Homo sapiens

<400> SEQUENCE: 27

Lys Ser Ser Ser Tyr Ser Lys Gln Phe Thr Ser Ser Thr Ser Tyr Asn
1               5                   10                  15

Arg Gly Asp Ser Thr Phe Glu Ser Lys Ser Tyr Lys
            20                  25

<210> SEQ ID NO 28
<211> LENGTH: 16
<212> TYPE: PRT
<213> ORGANISM: Homo sapiens

<400> SEQUENCE: 28
```

```
Ser Gln Gly Val Asn Asp Asn Glu Glu Gly Phe Phe Ser Ala Arg Gly
1               5                   10                  15

<210> SEQ ID NO 29
<211> LENGTH: 13
<212> TYPE: PRT
<213> ORGANISM: Homo sapiens

<400> SEQUENCE: 29

Met Ser Glu Thr Ser Arg Thr Ala Phe Gly Gly Arg Arg
1               5                   10

<210> SEQ ID NO 30
<211> LENGTH: 17
<212> TYPE: PRT
<213> ORGANISM: Homo sapiens

<400> SEQUENCE: 30

Leu Ser His Leu Val Leu Gly Val Val Ser Leu His Ala Ala Val Ser
1               5                   10                  15

Thr

<210> SEQ ID NO 31
<211> LENGTH: 15
<212> TYPE: PRT
<213> ORGANISM: Homo sapiens

<400> SEQUENCE: 31

Gly Ser Pro Met Tyr Ser Ile Ile Thr Pro Asn Ile Leu Arg Leu
1               5                   10                  15

<210> SEQ ID NO 32
<211> LENGTH: 13
<212> TYPE: PRT
<213> ORGANISM: Homo sapiens

<400> SEQUENCE: 32

Glu Asn Lys Glu Val Glu Glu Glu Arg Ile Ala Gly Thr
1               5                   10

<210> SEQ ID NO 33
<211> LENGTH: 15
<212> TYPE: PRT
<213> ORGANISM: Homo sapiens

<400> SEQUENCE: 33

Glu Asn Lys Glu Val Glu Glu Glu Arg Ile Ala Gly Thr Glu Gly
1               5                   10                  15

<210> SEQ ID NO 34
<211> LENGTH: 15
<212> TYPE: PRT
<213> ORGANISM: Homo sapiens

<400> SEQUENCE: 34

Glu Asn Lys Glu Val Glu Glu Glu Arg Ile Ala Gly Thr Glu Gly
1               5                   10                  15
```

METHODS AND KITS FOR PREDICTING A RESPONSE TO AN ERYTHROPOIETIC AGENT

RELATED APPLICATIONS

This application is a continuation application of U.S. application Ser. No. 13/167,478, filed Jun. 23, 2011, and now U.S. Pat. No. 9,057,731, and which claims priority from U.S. Provisional Application Ser. No. 61/357,843, filed Jun. 23, 2010, the entire disclosures of which are incorporated herein by this reference.

GOVERNMENT INTEREST

This invention was made with U.S. Government support under Grant Numbers P30ES014443, DK085673-01, DK077331, and DK072085 awarded by the National Institutes of Health; Grant Number DE-FG02-05ER6406 awarded by the U.S. Department of Energy; and individual Merit Awards awarded by the Department of Veterans Affairs to Drs. Michael E. Brier and Jon B. Klein. The government has certain rights in this invention.

TECHNICAL FIELD

The presently-disclosed subject matter relates to methods and kits for predicting a response to an erythropoietic agent in a subject. In particular, the presently-disclosed subject matter relates to methods and kits for predicting a response to an erythropoietic agent that are based on determining an amount of one or more peptide biomarkers in a biological sample from a subject.

BACKGROUND

The production of red blood cells, or erythropoiesis, is regulated by the sensing of the oxygen carrying capacity of the blood by the kidney and the subsequent production and release of erythropoietin (EPO). In normal individuals, that production and release of EPO allows hemoglobin (Hb) concentrations to be maintained at normal levels. In many patient populations, however, the administration of exogenous EPO is required to maintain Hb concentrations above 10 g/dL. These patient populations are diverse and include patients with chronic renal disease, HIV-infection, and cancer.

EPO is a glycoprotein hormone that exerts its erythropoietic effect through the EPO receptor (EpoR) and, as such, there is a series of both extra and intracellular events that must occur for EPO to regulate red blood cell production. Along these lines, and central to the current discussion of erythropoietic agents such as EPO, it has been observed that certain patients respond normally to pharmacologic concentrations of EPO (good responders), while other patients do not respond to typical pharmacologic concentrations (poor responders). Patients that are poor responders to EPO may be at risk for increased morbidity and mortality (1). Indeed, it has been further observed that the inability of these patients to reach a target hemoglobin concentration, in combination with the increased epoetin-α dose that must typically be administered, places these patients at an increased risk of death, myocardial infarction, congestive heart failure, or stroke (2).

Many factors may cause a poor response to an erythropoietic agent, such as EPO, including inadequate doses of the agent, functional or absolute iron deficiency, blood loss, infection, inflammation, secondary hyperparathyroidism, aluminum toxicity, hemolysis, malignancies, hematologic disorders, AIDS, pregnancy, and vitamin deficiency (3). Cytokines (IL-1, IL-6, interferon-γ, tumor necrosis factor), hepcidin, EpoR and the subsequent intracellular signaling have also been identified as potential regulators of EPO responsiveness (4, 5). Further, there is an interaction between IL-6 and hepcidin that is responsible for hypoferremia that may limit ESA response (6, 7), and soluble EpoR concentrations may be associated with EPO resistance in end stage renal disease (ESRD) (8, 9). To date, however, and despite the identification of factors that may cause different patients to respond differently to erythropoietic agents, biomarkers have yet to be identified that allow a patient's response to an erythropoietic agent to be effectively predicted.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments, and mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes methods and kits for predicting a response to an erythropoietic agent in a subject. In some embodiments of the presently-disclosed subject matter, a method for predicting a response to an erythropoietic agent in a subject is provided that includes the steps of: (a) providing a biological sample from the subject; and (b) determining an amount in the sample of at least one peptide selected from the group consisting of SEQ ID NOS: 1-17. In certain embodiments, the amount of the at least one peptide selected from SEQ ID NOS: 1-17, if present in the sample, is then compared to a control level of the at least one peptide and, if there is a measurable difference in the amount of the at least one peptide in the sample as compared to the control level, the comparison can be used to predict whether a subject is going to have a good response or a poor response to the erythropoietic agent.

In some embodiments, the methods of the presently-disclosed subject matter further comprise the step of determining whether there is a measureable difference in the amount of the at least one peptide in the sample as compared to the amount of the at least one peptide in a known good responder and/or a known poor responder, as an indicator of the subject's predicted response. In some embodiments, an amount of the erythropoietic agent administered to the subject is selected or modified based on the determined amount of the at least one peptide.

In some embodiments of the diagnostic methods described herein, the at least one peptide is selected from the group consisting of SEQ ID NOS: 1-14, and the subject is predicted to have a good response to the erythropoietic agent if there is a measurable difference in the amount of the at least one peptide selected from SEQ ID NOS: 1-14 as compared to the control level of the peptide. In other embodiments, the at least one peptide is selected from the group consisting of SEQ ID NOS: 15-17, and the subject is predicted to have a poor response to the erythropoietic agent if there is a measurable difference in the amount of the at least one peptide selected from SEQ ID NOS: 15-17 as compared to the control level of the peptide.

In other embodiments of the presently-disclosed subject matter, a method for determining whether to modify the amount of an erythropoietic agent being administered to the subject is provided. In some embodiments, an exemplary method for determining whether to modify an amount of an erythropoietic agent that is administered to a subject includes the steps of: (a) providing a series of biological samples over a time period from the subject; and (b) analyzing the series of biological samples to determine an amount in each of the biological samples of at least one peptide selected from the group consisting of SEQ ID NOS: 1-17. In some embodiments, the method further comprises comparing any measurable change in the amounts of the at least one peptide in each of the biological samples to thereby determine whether to modify the amount of the erythropoietic agent administered to the subject. In some embodiments, the series of biological samples comprises a first biological sample collected prior to modifying the amount of the erythropoietic agent administered to the subject and a second biological sample collected after modifying the amount of the erythropoietic agent administered to the subject.

In some embodiments of the presently-disclosed methods for determining whether to modify the amount of an erythropoietic agent being administered to the subject, the at least one peptide is selected from the group consisting of SEQ ID NOS: 1-14, and the amount of the erythropoietic agent administered to the subject is decreased if there is a measurable difference in the amount of the at least one peptide selected from SEQ ID NOS: 1-14 as compared to the control level. In other embodiments, the at least one peptide is selected from the group consisting of SEQ ID NOS: 15-17, and the amount of the erythropoietic agent administered to the subject is increased if there is a measurable difference in the amount of the at least one peptide selected from SEQ ID NOS: 15-17 as compared to the control level.

In some embodiments of the methods described herein, the subject has kidney disease, anemia, or cancer. Further, in some embodiments, the biological sample from the subject comprises blood, plasma, serum, or urine. In some embodiments, the subject is human.

With regard to the step of determining an amount in the sample of at least one peptide, in some embodiments, determining the amount in the sample of the at least one peptide comprises applying the biological sample to a device capable of affecting detection of the at least one peptide. In some embodiments, determining the amount in the sample of the at least one peptide comprising using mass spectrometry (MS) analysis, immunoassay analysis, or both to determine the amount of the at least one peptide. The MS analysis can comprise, in some embodiments, matrix-assisted laser desorption/ionization (MALDI) time-of-flight (TOF) MS analysis. In some embodiments, the immunoassay analysis comprises an enzyme-linked immunosorbent assay (ELISA).

In further embodiments of the presently-disclosed subject matter, an antibody or fragment thereof is provided that specifically recognizes a peptide selected from the group consisting of SEQ ID NOS: 1-17.

In still other embodiments of the presently-disclosed subject matter, a kit for predicting a response to an erythropoietic agent is provided. In some embodiments, a kit for predicting a response to an erythropoietic agent in a subject is provided that comprises one or more antibodies or fragments thereof that specifically recognize a peptide selected from the group consisting of SEQ ID NOS: 1-17. In some embodiments of the kits, the antibody is bound to a substrate and, in some embodiments, the kits can further include instructions for using the kit. In some embodiments, a plurality of different antibodies can be included in the kits such that each kit includes a number of antibodies capable of detecting a number of the peptides of SEQ ID NOS: 1-17.

Further features and advantages of the presently-disclosed subject matter will become evident to those of ordinary skill in the art after a study of the description, figures, and non-limiting examples in this document.

BRIEF DESCRIPTION OF THE DRAWINGS

FIG. 1A) and hepcidin (FIG. 1B) concentrations in subjects, where the concentrations are displayed according to group (good vs. poor responder) and gender.

FIGS. 2A-2B are graphs showing serum concentrations of IL-6 (FIG. 2A), IL-7 (FIG. 2B), IL-8 (FIG. 2C), IL-10 (FIG. 2D), and TNF-alpha (FIG. 2E) found in sample from subjects, where the concentrations are displayed according to group (good vs. poor responder) and gender.

FIGS. 5A-5D are graphs (FIGS. 5A-5B) and an image of an immunoblot (FIGS. 5C-5D) showing the distribution of a serum cysteine/histidine rich 1 (CYHR1) fragment and protein levels associated with erythropoietic agent responsiveness, where peptide abundance data was extracted from aligned MS data sets and peptide spectral abundance was calculated from the MS ion cluster area, where vertical scatter plots (mean±SEM) for the differences in serum abundance for one CYHR1 fragment (FIG. 5A) and for densitometry measurements of circulating OSMRβ (FIGS. 5B-5C) illustrate significant differences in abundance between good responder and poor responder groups, and where the specificity of the CYHR1 antibody was confirmed using immunogen competition experiments (FIG. 5D) where the primary antibody was pre-incubated with a 10-fold excess of synthetic immunogen before applying it to a freshly blotted and blocked membrane.

BRIEF DESCRIPTION OF THE SEQUENCE LISTING

Figure 1A:
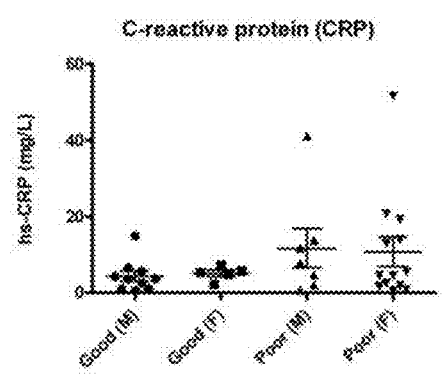
FIGS. 1A-1B are graphs showing serum C-reactive protein (CRP.
Figure 1B:
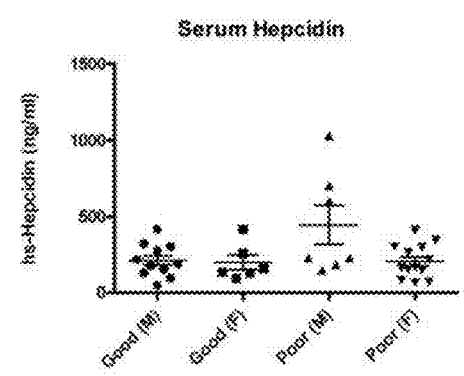

SEQ ID NOS: 1-10 are amino acid sequences of peptide fragments of a fibrinogen alpha chain protein;

SEQ ID NO: 11 is an amino acid sequence of a peptide fragment of a fibrinogen beta chain protein;

SEQ ID NO: 12 is an amino acid sequence of a peptide fragment of a coagulation factor XIII A chain protein;

SEQ ID NO: 13 is an amino acid sequence of a peptide fragment of a cysteine and histidine-rich protein 1 protein;

SEQ ID NO: 14 is an amino acid sequence of a peptide fragment of a complement C3 protein; and SEQ ID NOS: 15-17 are amino acid sequences of peptide fragments of an oncostatin-M specific receptor subunit beta protein.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a peptide" includes a plurality of such peptides, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

The terms "polypeptide", "protein", and "peptide", which are used interchangeably herein, refer to a polymer of the 20 protein amino acids, including modified amino acids (e.g., phosphorylated, glycated, etc.) and amino acid analogs, regardless of size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein", "polypeptide" and "peptide" are used interchangeably herein when referring to a gene product and fragments thereof. Thus, exemplary polypeptides include gene products, naturally occurring proteins, homologs, orthologs, paralogs, fragments and other equivalents, variants, fragments, and analogs of the foregoing.

The terms "polypeptide fragment" or "fragment", when used in reference to a polypeptide, refers to a polypeptide in which amino acid residues are absent as compared to the full-length polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. When the term "peptide" is used herein, it is intended to include the full-length peptide as well as fragments of the peptide. Thus, an identified fragment of a peptide (e.g., by mass spectrometry) is intended to encompass the fragment as well as the full-length peptide. As such, determining an amount of a biomarker in a sample can include determining an amount of the full-length biomarker polypeptide, modified variants, and/or fragments thereof.

Current biomarkers of hemoglobin (Hb) response to erythropoietic agents are primarily measurements of inflammation and iron availability. While these measurements remain important factors in monitoring a particular individual's response to an erythropoietic agent, the measurements do not address all of the aspects of a response to an erythropoietic agent and, as such, they can not effectively be used to predict whether an individual will exhibit a good or poor response to the administration of an erythropoietic agent. To that end, the presently-disclosed subject matter is based, at least in part, on the discovery of peptide biomarkers that can be obtained from a biological sample from a subject and effectively utilized to predict the subject's response to an erythropoietic agent and to determine whether to administer a specific dose of an erythropoietic agent to that subject or to modify a dose that the subject is already receiving.

In some embodiments, the presently-disclosed subject matter thus provides methods and systems for predicting a response to an erythropoietic agent in a subject, and for determining whether to modify an amount of an erythropoietic agent being administered to a subject, by identifying at least one biomarker in a biological sample from a subject. In some embodiments, the at least one biomarker is a peptide biomarker, or a fragment thereof, selected from the following Table 1:

TABLE 1

Peptide Biomarkers for Prediction of Responses to Erythropoietic Agents.

| SEQ ID NO: | Observed Mass (m/z) | Parent Protein Name | Amino Acid Amino Acid Sequence | Post-translational Modification | Mascot MOWSE | Paragon Unused Score |
|---|---|---|---|---|---|---|
| | | Freely Soluble | Increase Serum Abundunce with Hyper-response | | | |
| 1,18 | 1194.521 | Fibrinogen alpha chain | D.SGEGDFLAEGGGV.R | | 46 | 14 |
| 2,19 | 1399.623 | Fibrinogen alpha chain | S.GEGDFLAEGGGVR.G | (N-term + 136.16) | 116$ | |
| 3,20 | 1463.656 | Fibrinogen alpha chain | A.DSGEGDFLAEGGGVR.G | | | 14.0 |
| 4,21 | 1481.653 | Fibrinogen alpha chain | A.DSGEGDFLAEGGGVR.G | Phe → Tyr@7 | 132 | 14 |
| 5,22 | 1534.689 | Fibrinogen alpha chain | D.ADSGEGDFLAEGGGVR.G | | | 14.0 |
| 6,23 | 1534.689 | Fibrinogen alpha chain | D.SGEGDFLAEGGGVR.G | (N-term + 183.98) | 93$ | |
| 7,24 | 2466.054 | Fibrinogen alpha chain | S.SSYSKQFTSSTSYNRGDSTFES.K | | 55 | 14 |
| 8,25 | 2553.101 | Fibrinogen alpha chain | K.SSSYSKQFTSSTSYNRGDSTFES.K | | 75 | 14 |
| 9,26 | 2768.252 | Fibrinogen alpha chain | K.SSSYSKQFTSSTSYNRGDSTFESKS.Y | | 115 | 14 |
| 10,27 | 2931.292 | Fibrinogen alpha chain | K.SSSYSKQFTSSTSYNRGDSTFESKSY.K | | 63 | 14 |
| 11,28 | 1552.673 | Fibrinogen beta chain | S.QGVNDNEEGFFSAR.G | Gln → pyro-Glu@N-term | | 27 |
| | | Serum Protein Bound | | | | |
| 12,29 | 1210.582 | Coagulation factor XIII A Chain | M.SETSRTAFGGR.R | Acetyl@N-term | | 2.0 |
| 13,30 | 1488.800 | Cysteine and histidine-rich protein 1 | L.SHLVLGVVSLHAAVS.T | | | 1.3¶¶ |
| 14,31 | 1504.82 | Complement C3 | G.SPMYSIITPNILR.L | | 46 | 2 |
| | | Freely Soluble | | | | |
| 15,32 | 1273.633 | Oncostatin-M specific receptor subunit beta | E.NKEVEEERIAG.T | | 50 | 2.1 |
| 16,33 | 1549.744 | Oncostatin-M specific receptor subunit beta | E.NKEVEEERIAGTE.G | (C-term + 45.99) # | 48 | |
| 17,34 | 1664.801 | Oncostatin-M specific receptor subunit beta | E.NKEVEEERIAGTE.G | (T(12) + 161.02) | 49 | |

**Amino acid sequence is presented using Paris Convention guidelines for presenting proteomics data. The proteolytic excision sites are offset with periods. Amino acids within periods comprise the amino acid sequence for the observed peptide biomarker and are included as SEQ ID NOS: 1-17. SEQ ID NOS: 18-34 include the amino acid sequence for the peptide biomarkers as well as the amino acid residues outside of the periods.
$Matrix Science Mascot MOWSE Score following post-hoc error tolerant analysis.
Additional mass of 45.99 reflects addition of two sodium ions.
¶Protein Pilot Paragon Confidence Interval scoring for the protein and the peptides listed were 99% (Unused Score > 2.0) with simultaneous adjustment for decoy data base analysis and removal of false positive identifications.
¶¶Protein Pilot Paragon Confidence Interval scoring was 95% (Unused Score = 1.3) with simultaneous adjustment for decoy data base analysis and removal of false positive identifications.

In some embodiments of the exemplary human biomarkers included in Table 1 above, the core amino acid sequence can optionally be detected with additional masses added to the N- or C-terminus of the recited peptides. For example, in some embodiments, an additional mass (m/z) of about 136.16 can be added to the α-amino group of the N-terminus glycine residue in SEQ ID NO: 2. As another example, in certain embodiments, the sequence of SEQ ID NO: 6 can further include a mass of about 183.98 that is added to the N-terminal serine residue.

Further, the exemplary human biomarkers included in Table 1 above are not intended to limit the present subject matter to human polypeptide biomarkers or mRNA biomarkers only. Rather, the present subject matter is intended to encompass biomarkers across animal species that are capable of being used to predict a response to an erythropoietic agent in a subject. In addition, standard gene/protein nomenclature guidelines generally stipulate human gene name abbreviations are capitalized and italicized and protein name abbreviations are capitalized, but not italicized. Further, standard gene/protein nomenclature guidelines generally stipulate mouse, rat, and chicken gene name abbreviations italicized with the first letter only capitalized and protein name abbreviations capitalized, but not italicized. In contrast, the gene/protein nomenclature used herein when referencing specific biomarkers uses all capital letters for the biomarker abbreviation, but is intended to be inclusive of genes (including mRNAs and cDNAs) and proteins across animal species.

A "biomarker" is a molecule useful as an indicator of a biologic state in a subject. With reference to the present subject matter, the biomarkers disclosed herein can be polypeptides that exhibit a change in expression or state, and which can be correlated to and used to predict a response to an erythropoietic agent in a subject. In addition, the biomarkers disclosed herein are inclusive of messenger RNAs (mRNAs) encoding the biomarker polypeptides, because measurement of a change in expression of an mRNA can be correlated with changes in expression of the polypeptide encoded by the mRNA. As such, determining an amount of a biomarker in a biological sample is inclusive of determining an amount of a polypeptide biomarker and/or an amount of an mRNA encoding the polypeptide biomarker either by direct or indirect (e.g., by measure of a complementary DNA (cDNA) synthesized from the mRNA) measurement of the mRNA.

In some embodiments of the presently-disclosed subject matter, a method for predicting a response to an erythropoietic agent in a subject is provided. In some embodiments, the method comprises providing a biological sample obtained from a subject; and determining an amount in the sample of at least one peptide selected from the group consisting of SEQ ID NOS: 1-17 (i.e., the peptide biomarkers of Table 1). In some embodiments, the method further includes comparing the amount of the at least one peptide in the sample, if present, to a control level of the at least one peptide, wherein the subject is predicted to have a good response or a poor response to the erythropoietic agent if there is a measureable difference in the amount of the at least one peptide in the sample as compared to a control level. In other embodiments, the method further includes determining whether there is a measurable difference in the amount of the at least one peptide in the sample as compared to the amounts of the peptides in a good responder and/or a poor responder as an indication of the subject's predicted response to the erythropoietic agent.

The terms "erythropoietic agent," "erythropoiesis stimulating agents," or "ESA(s)" are used interchangeably herein to refer to agents that are capable of stimulating red blood cell production. As such, the term "erythropoietic agent" is inclusive of erythropoietin (EPO), but is also inclusive of iron or iron attached to various carrier proteins, as well as various pharmaceutical preparations of EPO including, but not limited to, Epoetin, Procrit or Epogen or Eprex or ReliPoietin or Epokine or Shanpoietin (epoetin-alpha), Epoetin-alpha, neoRecormon or Betapoietin (epoetin-beta), Epoetin-beta, Aranesp (darbepoetin), Darbopoetin alfa, Mircera (methoxy polyethylene glycol-epoetin beta), Methoxy Polyethylene Glycol-Epoetin beta, Dynepo (Epoetin delta), Epoetin delta, Hematide (peginesatide) and formulations of pharmaceutical preparations such as HIF PHI (HIF prolyl hydroxylase inihibor FG-2216 by FibroGen, Inc.) that effect the biological activity of prolyl hydroxylation including, but not limited to, hypoxia inducible factor alpha or beta subunits.

The terms "predicting" and "predict," as used herein, refer to methods by which the skilled artisan can estimate and even determine how a subject will respond to the administration of an erythropoietic agent, including the administration of a particular dose of erythropoietin. The skilled artisan often makes such a prediction on the basis of one or more indicators, such as, for example, a biomarker of the presently-disclosed subject matter, the amount (including presence or absence) of which is indicative of how the subject will respond to the erythropoietic agent. In some embodiments, and as described in further detail below, the presence or absence of the biomarker can be used to categorize a subject as one who will display a positive or a sufficient response to the erythropoietic agent (i.e., a "good responder") or as one who will display a negative or an insufficient response to the erythropoietic agent (i.e., a poor responder).

In some embodiments of the presently-disclosed subject matter, whether a subject is a good responder or a poor responder is determined by using a calculated average EPO response index (ERI), which is defined as the erythropoietic agent (e.g., erythropoietin) dose divided by the resulting hemoglobin after 1-month of treatment with the agent. In some embodiments, a sufficient response to an erythropoietic agent (e.g., erythropoietin) can be described with reference to a subject who achieves a hemoglobin (Hb) of 11 grams per deciliter (g/dL) with a dose of 15,000 Units erythropoietin per week (ERI of 1.36 g/dL per 1000 U/week). In such embodiments, subjects that respond below an ERI of 1.36 g/dL per 1000 U/week can be categorized as good responders, while those subjects that respond above an ERI of 1.36 g/dL per 1000 U/week can be categorized as poor responders.

In some embodiments, along with a qualitative assessment of whether a subject will display a good or a poor response to an erythropoietic agent, it is also important to quantify how well a particular subject will respond to the administration of an erythropoietic agent in order to plan the most effective therapy. If a more accurate assessment can be made of a particular subject's ability to respond to an erythropoietic agent, appropriate therapy, and in some instances less severe therapy, for the subject can be chosen such that the subject can be administered a controlled dose of the erythropoietic agent in a regulated manner. In this regard, measurement of biomarker levels disclosed herein (e.g., peptide biomarkers of SEQ ID NOS: 1-17) can be useful in order to categorize subjects according to how well they will respond to an erythropoietic agent to determine who will benefit from particular therapies and doses, and differentiate from other subjects where alternative or additional therapies can be more appropriate. As such, "making a prediction" or "predicting", as used herein, is further inclusive of determining the level at which a particular subject will respond to an erythropoietic agent, which can allow for predicting a clinical outcome (with or without medical treatment), selecting an appropriate treatment (or whether treatment would be effective), or monitoring a current treatment and potentially changing the treatment, based on the measure of predictive biomarker levels disclosed herein.

Of course, the term "predict" does not refer to the ability to predict whether a subject will display a good or poor response to an erythropoietic agent with 100% accuracy. Instead, the skilled artisan will understand that the term "predict" refers to an increased probability that a certain course or outcome will occur; that is, that a course or outcome is more likely to occur in a subject exhibiting certain levels of a biomarker, when compared to those individuals exhibiting control levels of the biomarkers. For example, in individuals expressing the biomarkers (e.g., expressing them at an increased level), the chance of a given response may be about 3%. In certain embodiments, a prediction is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will also understand that associating a predictive biomarker with a predisposition to a particular response is a statistical analysis. For example, a biomarker level (e.g., quantity of expression in a sample) of greater than a control level in some embodiments can signal that a subject is more likely to respond to the administration of an erythropoietic agent than subjects with a level less than or equal to the control level, as determined by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In other embodiments, a threshold degree of change in the level of a biomarker of the presently-disclosed subject matter can be established, and the degree of change in the level of the biomarker in a biological sample can simply be compared to the threshold degree of change in the level. A preferred threshold change in the level for markers of the presently disclosed subject matter is about 5%, about 10%, about 15%, about 20%, about 25%, about 30%, about 50%, about 75%, about 100%, and about 150%. In yet other embodiments, a "nomogram" can be established, by which a level of a biomarker of the presently-disclosed subject matter can be directly related to an associated disposition towards a given response to an erythropoietic agent. The skilled artisan is acquainted with the use of such nomograms to relate two numeric values with the understanding that the uncertainty in this measurement is the same as the uncertainty in the marker concentration because individual sample measurements are referenced, not population averages.

In some embodiments of the presently-disclosed subject matter, multiple determinations of one or more peptide biomarkers can be made, and a temporal change in the biomarker can be used to determine whether to modify an amount of an erythropoietic agent that is being administered to the subject. In such an embodiment, for example, the levels of biomarkers may decrease or increase over time indicating that the subject's response to the erythropoietic agent is changing and that the amount of erythroipoietic agent being administered to the subject should be modified (i.e., changed) as well. Thus, the presently-disclosed subject matter provides, in some embodiments, a method for determining whether to modify an amount of an erythropoietic agent being administered to a subject. In some embodiments, the method comprises determining an amount of at least one biomarker associated with a response to an erythropoietic agent, such as for example at least one biomarker included in Table 1 (i.e., SEQ ID NOS: 1-17), in biological samples collected from the subject at a plurality of different time points and comparing the amounts of the at least one peptide in the samples collected at different time points. For example, a first time point can be selected and a second later time point can be selected. One or more biomarker levels can be measured in biological samples taken at the different time points and qualitative and/or quantitative differences noted. A change in the amounts of the biomarker levels from the first and second samples can be correlated with a change in the response to an erythropoietic agent in a subject (e.g., changes in the levels of red blood cells or changes in hemoglobin concentrations) and can then be used to determine whether the amount of the erythropoietic agent being administered to the subject should be modified.

The term "modify," and grammatical variations thereof, is used herein to refer to any changes or adjustments that can be made to the dose of an erythropoietin agent being administered to a subject. Determination and adjustment of a dose of an erythropoietic agent, as well as evaluation of when and how to make such adjustments, are known to those of ordinary skill in the art of medicine.

The terms "correlated" and "correlating," as used herein in reference to the use of the presently-disclosed biomarkers, refer to comparing the presence or quantity of the biomarker in a subject to its presence or quantity in subjects known to display a particular response to an erythropoietic agent, i.e. "good responders" or "poor responders." For example, a biomarker level in a biological sample can be compared to a level known to be associated with a specific response to an erythropoietic agent. The sample's biomarker level is said to have been correlated with the level of response that the subject will display to the erythropoietic agent; that is, the skilled artisan can use the biomarker level to determine whether the subject will be a good or a poor responder to the erythropoietic agent, and administer an appropriate dose of the agent to the subject. For example, based on the level of the biomarker and its comparison with a level of the biomarker known to be associated with a poor response, the skilled artisan may determine that the subject is a poor responder to erythropoietic agents and administer an increased dose of the agent to the subject. Alternatively, a sample's biomarker level can be compared to a control marker level known to be associated with a good response to the erythropoietic agent, and the amount of erythropoietic agent administered to the subject can be modified (e.g., decreased) accordingly.

With regard to the step of providing a biological sample from the subject, the term "biological sample" as used herein refers to any body fluid or tissue potentially comprising the biomarkers of the presently-disclosed subject matter (e.g., the peptide biomarkers of Table 1), including, but not limited to, blood, plasma, serum, or urine. In some embodiments, for example, the biological sample can be a blood sample, a serum sample, a plasma sample, or sub-fractions thereof.

With regard to the subjects from whom the sample is obtained, in some embodiments, the methods of the presently-disclosed subject matter are particularly useful in subjects having a particular disease for which the administration of erythropoietic agents are typically recommended. For example, in some embodiments, the subject has kidney disease, anemia (e.g., anemia of chronic disease), or cancer, each of which are known to those of ordinary skill in the art as diseases or conditions in which the amount of red blood cells and/or the concentrations of hemoglobin may fall below normal levels and thus require the administration of an erythropoietic agent.

"Kidney disease," as used herein refers to an acute or chronic injury to at least one kidney of a subject, and in particular renal tubular cell injury. Kidney injury can be confirmed by any of a number of measurable criteria known in the art, including but not limited to measurement of the level of microalbuminuria (MA) and renal function decline (e.g., by measuring glomerular filtration rate (GFR)) in a subject.

The term "anemia" is used herein to refer to a decrease in the amount of red blood cells in a subject and/or a decrease in the amount of hemoglobin in a subject as compared those exhibiting normal levels of red blood cells or hemoglobin. A decrease in the amount of red blood cells in a subject or a decrease in the amount of hemoglobin can be measured using any number of criteria and methods known to those or ordinary skill in the art. In some embodiments, the anemia that is observed in the subject is anemia of chronic disease, or anemia of inflammation, which is frequently observed during chronic illness (e.g., certain forms of kidney disease), and may be the result of the body of a subject's production of hepcidin or other regulators of iron metabolism.

The term "cancer" is used herein to refer to all types of cancer or neoplasm or malignant tumors found in animals, including leukemias, carcinomas, melanoma, and sarcomas. Examples of cancers are cancer of the brain, bladder, breast, cervix, colon, head and neck, kidney, lung, non-small cell lung, mesothelioma, ovary, prostate, sarcoma, stomach, uterus and Medulloblastoma.

Turning now to the step of identifying one or more biomarkers in the biological sample, various methods and devices known to those skilled in the art can be used to identify the one or more biomarkers in the provided biological sample. In some embodiments, the methods of the presently-described subject matter further comprise the step of applying the biological sample to a device capable of affecting detection of the at least one peptide. For example, as described in further detail below, in some embodiments, a technician can provide a biological sample (e.g., select or pick up) and can then apply that sample to a mass spectrometry device to determine an amount of biomarkers in the provided sample.

In some embodiments, determining the amount of biomarkers in samples comprises using an RNA measuring assay to measure mRNA encoding biomarker polypeptides in the sample and/or using a protein measuring assay to measure amounts of biomarker peptides in the sample.

In certain embodiments, the amounts of biomarkers can be determined by probing for mRNA of the biomarker in the sample using any RNA identification assay known to those skilled in the art. Briefly, RNA can be extracted from the sample, amplified, converted to cDNA, labeled, and allowed to hybridize with probes of a known sequence, such as known RNA hybridization probes (selective for mRNAs encoding biomarker polypeptides) immobilized on a substrate, e.g., array, or microarray, or quantitated by real time PCR (e.g., quantitative real-time PCR, such as available from Bio-Rad Laboratories, Hercules, Calif., U.S.A.). Because the probes to which the nucleic acid molecules of the sample are bound are known, the molecules in the sample can be identified. In this regard, DNA probes for one or more of nucleic acid sequences encoding a peptide biomarker of the presently-disclosed subject matter can be immobilized on a substrate and provided for use in practicing a method in accordance with the present subject matter.

With regard to determining amounts of biomarker polypeptides in samples, mass spectrometry and/or immunoassay devices and methods can be used to measure biomarker polypeptides in samples, although other methods are known to those skilled in the art as well. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Thus, in certain embodiments of the presently-disclosed subject matter, the biomarker peptides are analyzed using an immunoassay. The presence or amount of a biomarker (e.g., a peptide biomarker of Table 1) can be determined using antibodies or fragments thereof specific for each biomarker and detecting specific binding. For example, in some embodiments, antibodies are provided that specifically recognize a peptide selected from SEQ ID NOS: 1-17. Such antibodies are inclusive of antibodies that bind the full-length peptides or fragments thereof. In some embodiments, the antibody is a monoclonal antibody. (For further explanation and guidance with respect to the production and purification of antibodies against a given epitope, see, e.g., Kohler and Milstein, Nature 256:495 (1975); U.S. Pat. Nos. 4,172,124; 4,350,683; 4,363,799; 4,381,292; and 4,423,147. See also Kennett et al., Monoclonal Antibodies (1980) and references therein. Each of these references are incorporated herein by this reference.)

Any suitable immunoassay can be utilized in accordance with the presently-disclosed subject matter including, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies or fragments thereof specific for the markers is also contemplated by the presently-disclosed subject matter. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

In some embodiments, mass spectrometry (MS) analysis can be used alone or in combination with other methods (e.g., immunoassays) to determine the presence and/or quantity of the one or more biomarkers of interest (e.g., a peptide biomarker of Table 1) in a biological sample. In some embodiments, the MS analysis comprises matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers, such as for example triple quadrupole mass spectrometers. Methods for utilizing MS analysis, including MALDI-TOF MS and ESI-MS, to detect the presence and quantity of biomarker peptides in biological samples are known in the art. See, e.g., U.S. Pat. Nos. 6,925,389; 6,989,100; 6,890,763; and, Merchant, et al. (Am J Physiol Renal Physiol 2008, 295, F1254-1258) for further guidance, each of which is incorporated herein by this reference.

Although certain embodiments of the method only call for a qualitative assessment of the presence or absence of the one or more biomarkers in the biological sample, other embodiments of the method call for a quantitative assessment of the amount of each of the one or more biomarkers in the biological sample. Such quantitative assessments can be made, for example, using one of the above mentioned methods, as will be understood by those skilled in the art.

In certain embodiments of the method, a subject is predicted to have a good or a poor response to an erythropoietic agent upon identifying in a biological sample obtained from the subject certain of the biomarkers selected from SEQ ID NOS: 1-17. For example, in some embodiments, a subject is predicted to have a good response to the erythropoietic agent if there is a measureable difference (e.g., an increase) in the amount of one or more of the peptide biomarkers of SEQ ID NOS: 1-14 as compared to a control level of those biomarkers. In some embodiments, the subject is predicted to have a good response to the erythropoietic agent if there is a measurable difference (e.g., an increase) in the amount of the peptide of SEQ ID NO: 13. In other embodiments of the method, a subject is predicted to have a poor response to the erythropoietic agent if there is a measureable difference (e.g., an increase) in the amount of one or more of the peptide biomarkers of SEQ ID NOS: 15-17 as compared to a control level of those biomarkers.

As noted herein above, in certain embodiments of the presently-disclosed methods, it can be desirable to include a control sample that is analyzed concurrently with the biological sample, such that the results obtained from the biological sample can be compared to the results obtained from the control sample. Additionally, it is contemplated that standard curves can be provided, with which assay results for the biological sample can be compared. Such standard curves present levels of protein marker as a function of assay units, i.e., fluorescent signal intensity, if a fluorescent signal is used. Using samples taken from multiple donors, standard curves can be provided for control levels of the one or more markers in normal tissue.

It is also contemplated that the efficacy, accuracy, sensitivity, and/or specificity of the method can be enhanced by probing for multiple biomarkers in the biological sample. For example, in certain embodiments of the method, the biological sample can be probed for the peptide biomarker of SEQ ID NO: 13 and at least one marker selected from the peptides of SEQ ID NOS: 15-17. For another example, the biological sample can be probed for 2-5 markers selected from the peptide biomarkers of SEQ ID NOS: 1-17. For another example, the biologic sample can be probed for 6-10 markers selected from the peptide biomarkers of SEQ ID NOS: 1-17.

The analysis of biomarkers can be carried out separately or simultaneously with additional markers within one test sample. For example, several biomarkers can be combined into one test for efficient processing of a multiple of samples and for potentially providing greater predictive accuracy. In addition, one skilled in the art would recognize the value of testing multiple samples (for example, at successive time points) from the same subject. Such testing of serial samples can allow the identification of changes in biomarker levels over time. Increases or decreases in biomarker levels, as well as the absence of change in biomarker levels, can provide useful information about the subject's status that includes, but is not limited to, identifying any changes in response to an erythropoietic agent over time, the appropriateness of drug therapies, the effectiveness of various therapies, and identification of the subject's outcome, including risk of future events.

The analysis of biomarkers can be carried out in a variety of physical formats as well. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

As mentioned above, depending on the embodiment of the method, identification of the one or more markers can be a qualitative determination of the presence or absence of the biomarkers, or it can be a quantitative determination of the concentration of the biomarkers. In this regard, in some embodiments, the step of identifying the subject as being a good or a poor responder to an erythropoietic agent requires that certain threshold measurements are made, i.e., the levels of the one or more biomarkers in the biological sample exceed control levels. In certain embodiments of the method, the control level is any detectable level of the biomarker. In other embodiments of the method where a control sample is tested concurrently with the biological sample, the control level is the level of detection in the control sample. In other embodiments of the method, the control level is based upon and/or identified by a standard curve. In other embodiments of the method, the control level is a specifically identified concentration, or concentration range. As such, the control level can be chosen, within acceptable limits that will be apparent to those skilled in the art, based in part on the embodiment of the method being practiced and the desired specificity, etc.

Further provided, in some embodiments of the presently-disclosed subject matter, is a system for the analysis of biomarkers that comprises antibodies having specificity for one or more markers associated with a subject's response to an erythropoietic agent, including the peptide biomarkers of SEQ ID NOS: 1-17. Such a system can comprise devices and reagents for the analysis of at least one test sample. The system can further comprise instructions for using the system and conducting the analysis. Optionally, the systems can contain one or more reagents or devices for converting a marker level to a prediction of a response in a subject.

Still further provided, in some embodiments, are kits for predicting a response to an erythropoietic agent that comprise one or more antibodies or fragments thereof that specifically recognize a peptide selected from SEQ ID NOS: 1-17. In some embodiments, the one or more antibodies are bound to a substrate and, in some embodiments, the one or more antibodies comprise a plurality of antibodies. In other embodiments, the kits further include instructions for using the kit, such as instructions for using the kit to predict a response to an erythropoietic agent in a subject.

In yet further embodiments of the presently-disclosed subject matter, a method for screening for a compound useful for increasing red blood cell production is provided that comprises: providing a first subject and a second subject; administering a test compound to the second subject; obtaining a biological sample from the first subject and the second subject; determining an amount in the samples from the first subject and the second subject of at least one peptide selected from SEQ ID NOS: 1-17; and identifying the test compound as a compound useful for increasing red blood cell production based on a measurable difference in the amount of the at least one peptide in the sample of the second subject as compared to the first subject.

In further embodiments of the presently-disclosed subject matter, a method for determining and/or monitoring an amount of an erythropoietic agent administered to a subject is provided that comprises obtaining a biological sample from a subject administered or suspected of being administered an erythropoietic agent; determining an amount in the sample of at least one peptide selected from the group consisting of SEQ ID NOS: 1-17; and comparing the amount of the at least one peptide in the sample, if present, to a level of the at least one peptide known to be associated with a particular dose of the erythropoietic agent to thereby determine and/or monitor the amount of the erythropoietic agent administered to the subject. As would be recognized by those of ordinary skill in the art, such a method can be useful in monitoring erythropoietic agent dosing of subjects, including illicit dosing by subjects such as cyclists, Olympic athletes, and high school, collegiate, and/or professional athletes.

With respect to the presently-disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials and Methods for Examples 1-5

Human Subjects. The research protocol conformed to the Declaration of Helsinki and informed consent was obtained from each subject prior to participation in the study. The study was approved by the Institutional Review Boards for both the University of Louisville and the Louisville Veterans Administration Medical Center. Subjects were identified for participation in this study by determining their EPO responsiveness from dose and response data. EPO dose and hemoglobin data were collected over a 5 month period of treatment for all in-center hemodialysis patients in the Kidney Disease Program hemodialysis unit. For each combination of EPO dose and hemoglobin, an EPO response index (ERI) was calculated as the EPO dose divided by the resulting hemoglobin 1 month later. These data were averaged over the 5 months of collected data and a mean ERI and standard deviation were determined. The mean data were sorted in ascending order and subjects for the normal response group were selected from the lowest quintile group. Subjects for the resistant responder group were selected from the highest quintile group.

Subjects were asked to enroll based on their falling into either the upper or lower quintile and based on the absence of the following exclusion criteria: subjects were excluded if they: were inadequately dosed using an erythropoietic stimulating agent; were iron deficient; were anemic due to blood loss; had a chronic infection or inflammation; had secondary hyperparathyroidism; had aluminum toxicity; had hemolysis; had any malignancies or hematologic disorders; had AIDS; were pregnant; or, had a vitamin deficiency.

Samples and Sample Handling. Subjects that passed the screening described above were asked to donate 20 ml of blood for proteomic analysis following an informed consent process. The blood was collected in 2 to 10 ml red top vacutainer tubes prior to the initiation of the dialysis session, and was processed immediately for serum separation and stored in 0.5 ml aliquots at −80° C. until analyzed.

Peptides were isolated from serum using Vivaspin 2 (Sartorius AG, Gottingen, Germany) spin filtration devices housing 5,000 Dalton nominal molecular weight cutoff Hydrosart® (cellulosic) membranes (Sartorius AG, Gottingen, Germany). The sample handling approach yielded two low molecular weight peptidomic fractions: (a) freely soluble serum peptides; and (b) peptides bound to serum proteins. In this approach, 200 µL of each sample was loaded into Vivaspin 2 spin filtration device and spun at 3,000×g and 4° C. until 180 µL filtrate had been collected in the retentate cup. The filtrate from this step (fraction 1) contained the freely soluble peptides. The remaining 20 µL was diluted using 50 mM sodium phosphate/0.5 mM sodium EDTA, pH 7.4. The diluted sample was spun and concentrated down to 20 µL. The filtrate of this step was discarded. The process was repeated twice. The final sample was diluted back to 200 µL with 50 mM sodium phosphate/0.5 mM sodium EDTA, pH 7.4. To this solution, a stock solution of 8 M urea/0.89 M β-mercaptoethanol was added and used to denature and reduce all soluble protein. The final concentration of these reagents was 6 M urea and 0.667 M β-mercaptoethanol. This solution was then left to equilibrate for 2 h at room temperature. Subsequently, the solution was spun at 3,000×g and 4° C. until at least 120 µL filtrate had been collected in the retentate cup. The filtrate from this step (fraction 2) contained the serum protein bound peptides. These peptide fractions were lyophilized, redissolved into water, and then cleaned (concentrated and desalted) using a C18 reversed-phase cartridge (Michrom Bioresource, Auburn, Calif.) and acetonitrile and formic acid solutions.

Peptidomic Analyses. Isolated peptides were analyzed using the method of Merchant, et al (26). Briefly, isolated peptides were analyzed using reversed-phase (RP) capillary-high performance liquid chromatography (capHPLC), robotically spotted onto archivable MALDI-TOF MS plates (Opti-TOF plates), and MALDI-TOF MS data was acquired using an Applied Biosystems (Foster City, Calif.) AB4700 Proteomics Analyzer operating in reflectron mode. LC MALDI-TOF MS ion chromatograms were constructed using Data Explorer software (Applied Biosystems, Foster City, Calif.) and then exported as peak list text files and used for determination of differential peptide abundance. Additionally, individual LC-MS spectra were concatenated to produce serum (FX1 or FX2) peptide LC-MALDI-TOF MS ion chromatogram per each sample fraction analyzed.

Analysis of Serum Peptide Abundance. Data from LC-MALDI-TOF MS ion chromatograms were extracted in the form of integrated signal area for the peptide isotopic series (area under the curve, AUC) from the AB4700.t2d files using Data Explorer (Applied Biosystems, Foster City, Calif.) software and exported to MarkerView (Applied Biosystems, Foster City, Calif.) software to chromatographically align and array the tabulated peptide peak list data. Three LC fractions collected prior to initiating the RP elution gradient and following re-equilibration of the column from 100% solvent B to 100 solvent A were used to establish a null peptide mass list. These masses were subtracted from the aggregate data set. For purposes of statistical comparison, all peptide masses not appearing in a minimum of 80% (n=28) samples were excluded from further analysis. The remaining peptides were compared by unpaired student's t-test. Peptides having p-values less than 0.05 (p<0.05) were considered significant. To illustrate selection of peptide for further analysis, the data for peptides with a P-value<0.05 and a fold expression difference of 133% are illustrated. This approach provided a method to compare the level of statistical significance of differential protein or peptide abundance and the fold over- or under-expression of proteins or peptides given a set of treatment conditions.

Computer Assisted Tandem-MS Data Analysis. Candidate peptide m/z values selected from the statistical analyses were further investigated using tandem MS methods to better understand their importance in EPO responsiveness. The selected peptide masses were used to establish a MALDI ion inclusion list and were fragmented using the AB4700 Proteomics Analyzer in TOF/TOF mode using 1KeV collision energy, collision induced dissociation (CID) and atmospheric gases (medium pressure). Final fragmentation data were collected as averaged data from 1500 laser shots.

The peptide fragmentation information was searched against the Swiss-Prot database using Matrix Science Mascot software (version 2.1) and using the Paragon algorithm of Protein Pilot to identify peptides with the highest correlative amino acid sequence. The Mascot algorithm was used to search the MS/MS datasets assuming no post-translational modifications. The Paragon algorithm was used in addition to the Mascot algorithm due to the ability to simultaneously search the unassigned data for amino acid substitutions (such as resulting from single nucleotide polymorphisms) and for more than 130 post translational modifications. Criteria used for Mascot analysis were: (a) unconstrained proteolytic search (no enzyme fragmentation criteria stipulated); (b) Swiss Protein database (20100119, 514212 sequences, 180900945 residues), Homo sapiens taxonomy (20355 sequences); (c) 0.15 Da mass accuracy for precursor peptides; and, (d) 0.3 Da mass accuracy for peptide fragment ion mass measurement. The resulting search yielded the likelihood of peptide homology or identity by a given total ion MOWSE (Molecular Weight Search) score of 47 or greater. Criteria used for the Protein Pilot (version 3.0, revision number 114732) and Paragon algorithm (version 3, revision 113442) analysis were: (a) uniprot_sprot.fasta database (revision of UniProt release 15.0); (b) an identification focus of both biological modifications and amino acid substitutions; and, (c) an Unused ProtScore (Conf)>: 0.05 and Competitor Error Margin (ProtScore) ≥2.0. All Protein Pilot Paragon analyses were conducted using simultaneous analysis against a reversed SwissProt database and automated filtering and retaining of peptides scoring with q-values (false discovery rate filter)≤0.10. Two oncostatin M receptor (OSMR) peptides were assigned a mass value that are consistent with modifications including di-sodiation (+45.99 m/z) of peptide 1549.774 and O-glucosamine (O-GlcN) modification (+161.02 m/z) of peptide 1664.801 at threonine-539 using the Delta Mass database as a guide for identity assignment. To further explore the likelihood of an O-GlcN modification to Thr-539, the proposed peptide amino acid sequence plus 30 residues on the flanking N- and C-terminal amino acid sequence were analyzed for the potential to have O-glycan modification using the NetOGlyc tool. The best general predictor score (G-score) exceeded 0.5 for one threonine within this sequence. The G-score for this residue, Thr-539, exceeds the threshold value indicating a significant likelihood of a site being modified by O-glycosylation.

Immunoblot Analyses for Serum Protein Abundance. In order to examine if the increased serum abundance of oncostatin M receptor beta subunit (OSMRβ) and of cysteine and histidine-rich protein-1 (CYHR1) fragments resulted from increased serum OSMRβ and CYHR1 serum protein abundance, immunoblotting experiments using native (denaturing) and Laemmli (reducing/denaturing) sample buffers were conducted. These analyses were conducted using polyclonal antibodies raised to either full length human OSMRβ (Abcam Inc., Cambridge, Mass.; cat. no. ab67805) and an internal epitope of human CYHR1 (Santa Cruz Biotechnology, Inc., Santa Cruz, Calif.; sc-87664). The expression of OSMRβ and CYHR1 were examined using previously unthawed, contemporaneous aliquots of the serum sample set used for peptidomic analyses.

In brief, serum samples were mixed with Laemmli Sample Buffer (Invitrogen, Carlsbad, Calif.) and β-mercaptoethanol was added as needed. The samples were then heated to 70° C. for 10 min. Serum samples for OSMRβ immunoblot analysis were separated using large format 10-20% Tris-Glycine gels (Jule Inc., Milford, Conn.) using tris-glycine-SDS buffer. Serum samples for CYHR1 immunoblot analysis were separated using small format NuPAGE 4-12% Bis-Tris gels (Invitrogen, Carlsbad, Calif.). The proteins were transferred to 0.45 µm nitrocellulose membrane (Whatman, Dassel, Germany) for 90 min at 30 V using Tris-NuPAGE transfer buffer (Invitrogen, Inc.) with 20% methanol for OSMRβ immunoblot analysis or 35 V at 150 mA for 35 Vh for CYHR1 immunoblot analysis.

After transfer, membranes used for OSMRβ immunoblot experiments were blocked with 1% skim milk for overnight, rinsed three times with TTBS (20 mM Tris-buffered saline/ 0.1% Tween 20) and incubated overnight with mouse anti-OSMRβ antibody (1:1000 in TTBS) at 4° C. Membranes were washed with TTBS. Following 1 hour incubation with horse radish peroxidase (HRP) conjugated secondary goat anti-mouse (1:10,000 in 5% milk), membranes were developed using West Pico Chemiluminescence substrate (Pierce, Rockford, Ill.). Membranes used for CYHR1 immunoblot experiments were blocked with 5% skim milk for overnight, rinsed three times with TTBS (20 mM Tris-buffered saline/ 0.1% Tween 20) and incubated overnight with goat anti-CYHR1 antibody (1:1,000 in 1% skim milk). HRP conjugated secondary goat anti-mouse (1:10,000 in 5% milk) membranes were developed using West Pico Chemiluminescence substrate (Pierce, Rockford, Ill.). Films were imaged and densitometry measurements acquired and compared. For CYHR1, additional peptide blocking experiments using the protein immunogen were conducted to examine monospecific binding of the antibody to antigen. The CYHR1 antibody (1 µg) was incubated with 10 µg immunogen for 2 h at room temperature prior to application on the blocked nitrocellulose membrane.

Analysis of Serum Markers of Inflammation and Iron Status. High sensitivity C-reactive protein (hs-CRP) measurements in patient serum samples were made using the Immulite 1000 High Sensitivity CRP kit by Siemens according to the manufacturer's guidelines. The Immulite 1000 High Sensitivity CROP is a solid-phase chemiluminescent immunometric assay. The samples were diluted 1:101 with sample diluent then admixed and co-incubated for 30 minutes with solid phase bead (coated with primary antibody (anti-CRP) capture reagent), monoclonal murine anti-CRP monoclonal antibody and an alkaline phosphatase conjugated polyclonal rabbit anti-mouse antibody. The unbound patient sample and antibody complexes were removed by centrifugal wash. A chemiluminescent substrate was added to the test unit containing the bead and the signal generated was accepted as proportional to the bound enzyme.

Hepcidin-25 peptide measurements were made using the hepcidin-25 peptide enzyme immunoassay kit (EIA) S-1337 (Bachem Group, Torrance, Calif.) and using the hepcidin-25 standard LEAP1 from Peptides International, Inc. (Louisville, Ky.) as a positive control. Serum was diluted 1:40 using EIA buffer provided in kit, and 50 µl of both diluted serum samples and hepcidin-25 standard were added to the antiserum pre-coated plated for 2 hours at room temperature. A 25 µl aliquot of biotinylated antiserum (tracer) was then added to the plated for competitive binding of hepcidin overnight at 4° C. The captured biotinylated tracer was subsequently bound by streptavidin-conjugated horseradish peroxidase (SA-HRP), and the intensity of color developed after adding the substrate TMB was inversely proportional to the concentration of hepcidin in samples. The plate was read at 450 nm within 10 minutes of adding stop solution. The R-squared was 0.9967 for LEAP1 positive control peptide from 0-50 ng/ml using sigmoid regression while 0.9969 for the hepcidin-25 standard provided in Bachem EIA kit. The coefficient of variation (CV) for a given hepcidin-25 concentration of 1.56 ng/ml was 3.49% intra-assay and 3.43% inter-assay.

Statistical Analysis. Statistical analysis was performed using PASW Statistics 18. Comparisons of proportions, means, and means by gender were done by Pearson chi square, t-test and analysis of variance, respectively. When multiple fragments of the same parent protein were analyzed a Bonferroni correction was applied to address the problem of multiple comparisons and the data were analyzed as the sum of all fragment abundances. The ability of the identified biomarkers to discriminate between groups was analyzed by ROC curve.

Example 1

Characteristics of the Study Population

The demographics of the subjects enrolled in the study are shown in Table 2. There were significant differences in ESA dose and average EPO response index (ERI), defined as the EPO dose divided by the resulting hemoglobin 1 month later, between the two study groups. The distribution of gender between groups was different but did not reach statistical significance.

TABLE 2

Demographics of the Subject Population at Time of Sample Collection.

| | Good Responder | Poor Responder | p-value |
| --- | --- | --- | --- |
| Gender (m/f) | 10/5 | 7/13 | 0.06* |
| Hemoglobin (g/dL) | 11.5 ± 0.6 | 11.2 ± 1.1 | 0.4 |
| ESA Dose (U/treatment) | 1467 ± 673 | 8392 ± 5833 | <0.001 |
| Total Iron Dose (mg) | 953 ± 1187 | 2035 ± 1604 | 0.035 |
| Average ERI | 0.11 ± 0.036 | 0.87 ± 0.51 | <0.001 |
| Kt/V | 1.53 ± 0.25 | 1.58 ± 0.27 | 0.5 |
| Albumin (g/dL) | 3.9 ± 0.3 | 3.8 ± 0.3 | 0.3 |
| Ferritin | 767 ± 353 | 781 ± 416 | 0.9 |
| Tsat (%) | 30.5 ± 7.9 | 26.4 ± 16.5 | 0.4 |

*Pearson Chi-Square

The subjects' serum was assayed for C-reactive protein, serum hepcidin, IL-6, IL-7, IL-8, IL-10 and TNF-α. These data are shown in FIGS. 1A-1B and FIGS. 2A-2E. The results of the statistical analysis are shown in Table 3. The only difference detected was an interaction between group and gender in hepcidin, IL-6, and IL-8 where there appeared to be increased serum levels of hepcidin, IL-6 and IL-8 in male hypo responders.

TABLE 3

Statistical Analysis of the C-reactive Protein, Hepcidin and Cytokine Data.

| | p value | | |
| --- | --- | --- | --- |
| | Group | Gender | Interaction |
| CRP | 0.11 | 0.98 | 0.83 |
| Hepcidin | 0.068 | 0.11 | 0.043 |
| IL-6 | 0.71 | 0.18 | 0.018 |
| IL-7 | 0.37 | 0.26 | 0.59 |
| IL-8 | 0.57 | 0.58 | 0.046 |
| IL-10 | 0.11 | 0.19 | 0.16 |
| TNF-α | 0.51 | 0.97 | 0.76 |

Example 2

Serum Peptide Analysis

Figure 3A:
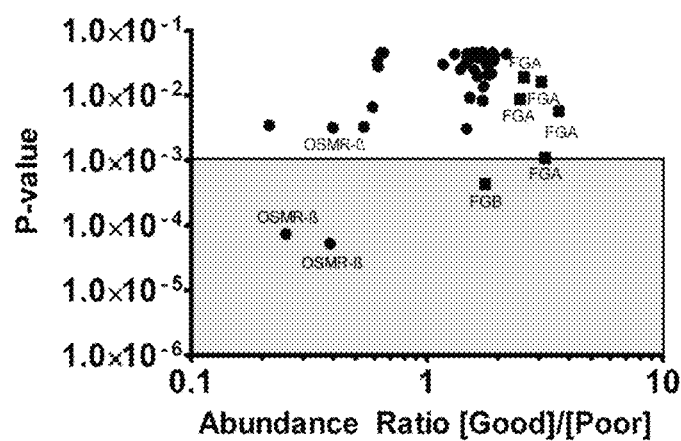
FIGS. 3A-3B are graphs showing a comparison of the size of the fold change in peptide abundance in good- to poor-responder serum samples to the statistical significance level, where, for peptides with t-test p-values less than 0.05, the ratio of the abundance (extracted from a 3-minute window of the LC-MALDI-TOF MS ion chromatogram) for the EPO good- to poor-responders were calculated, and where the t-test and ratio data are plotted using log-log graphing for each significant peptide from the freely soluble serum peptide and protein bound serum peptide fractions with the shaded regions denoting masses with a p-value less than 0.001.
Figure 3B:
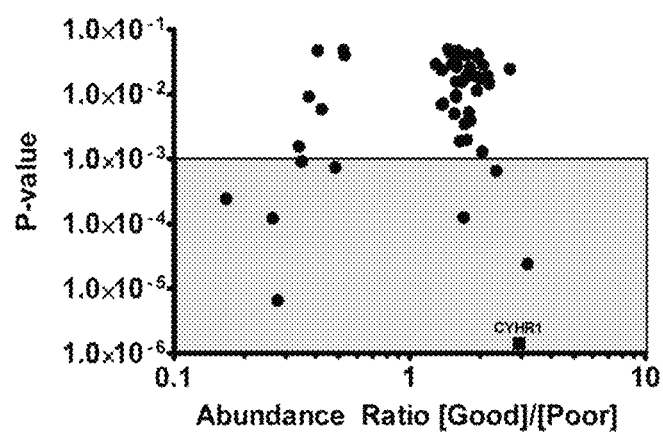

Most peptides were of low abundance and infrequently observed across all samples. A total of 939 freely soluble serum peptide masses were observed in 28 (82% of samples) or more serum samples. A total of 130 masses were observed in all 34 samples. By t-test, 40 peptides were observed to be differentially abundant with significance at the p≤0.05 level and 3 peptides at the p≤0.001 level (Table 4). A total of 558 protein bound serum peptide masses were observed in 28 or more serum samples. A total of 90 masses were observed in all 34 samples. By t-test, 51 peptides were observed to be differentially abundant with significance at the p≤0.05 level and 9 peptides at the p≤0.001 level (Table 5). To graphically illustrate these data, plots of significance (P-value) versus serum abundance differences in good-responder to poor-responder (serum abundance ratio) for freely soluble (FIG. 3A) and protein bound serum peptides (FIG. 3B) were constructed and annotated to indicate assignment of protein identities to respective data points. Mann and Kelleher have suggested fold-expression changes of 1.3 to 2.0 or greater to be meaningful for MS-based proteomics experiments (10). In the present data, defined by peptides with p-values≤0.05, 38 freely soluble serum peptides (95% total) and 50 protein bound serum peptides (98% total) demonstrated fold-abundance changes of 1.3 or greater. For purposes of emphasis, peptides estimated to have t-test P-values equal to or less than 0.001 are highlighted in FIG. 3 within the inset boxes.

TABLE 4

Peptides Identified as Differentially Abundant in Free Serum Peptidome (FX1).

| Peptide Mass to Charge Ratio (m/z) | Chromatographic (C18 Reversed Phase) Retention Time (min) | Observation Frequency (Out of 34 Samples) | Ttest | Mean abundance (Good Responder) | Mean abundance (Poor Responder) | Fold Abundance for [Good]/[Poor] | Rank |
|---|---|---|---|---|---|---|---|
| 1273.633 | 30 | 31 | 0.000053 | 24278 | 62525 | 0.39 | 1 |
| 1664.801 | 35 | 28 | 0.000074 | 5489 | 21769 | 0.25 | 2 |
| 1552.673 | 35 | 34 | 0.000436 | 80328 | 45578 | 1.76 | 3 |
| 2931.292 | 31 | 33 | 0.001107 | 115475 | 36514 | 3.16 | 4 |
| 852.885 | 38 | 32 | 0.003080 | 24214 | 16447 | 1.47 | 5 |
| 1549.774 | 36 | 28 | 0.003182 | 5110 | 12805 | 0.40 | 6 |
| 1393.727 | 35 | 34 | 0.003301 | 8937 | 16555 | 0.54 | 7 |
| 966.352 | 24 | 29 | 0.003479 | 12957 | 60430 | 0.21 | 8 |
| 2553.101 | 30 | 34 | 0.005737 | 90712 | 25069 | 3.62 | 9 |
| 1613.859 | 36 | 30 | 0.006602 | 3033 | 5162 | 0.59 | 10 |
| 1133.731 | 58 | 32 | 0.008351 | 15243 | 8843 | 1.72 | 11 |
| 2466.054 | 30 | 30 | 0.008865 | 22491 | 9077 | 2.48 | 12 |
| 1059.572 | 29 | 33 | 0.009226 | 125784 | 82602 | 1.52 | 13 |
| 987.643 | 56 | 28 | 0.013735 | 12726 | 7311 | 1.74 | 14 |
| 2768.252 | 29 | 34 | 0.016322 | 204777 | 67122 | 3.05 | 15 |
| 1481.653 | 30 | 34 | 0.019176 | 62729 | 24318 | 2.58 | 16 |
| 957.631 | 59 | 32 | 0.019904 | 17417 | 10620 | 1.64 | 17 |
| 1279.843 | 59 | 32 | 0.020860 | 9000 | 4946 | 1.82 | 18 |
| 1463.656 | 32 | 31 | 0.021406 | 26377 | 14029 | 1.88 | 19 |
| 1075.570 | 29 | 32 | 0.024467 | 48687 | 30613 | 1.59 | 20 |
| 1194.521 | 34 | 34 | 0.025702 | 35571 | 25570 | 1.39 | 21 |
| 1482.673 | 32 | 32 | 0.028119 | 5555 | 8952 | 0.62 | 22 |
| 740.293 | 38 | 34 | 0.030052 | 1107047 | 945822 | 1.17 | 23 |
| 3277.546 | 30 | 31 | 0.030507 | 17905 | 10006 | 1.79 | 24 |
| 1516.684 | 33 | 33 | 0.031415 | 15009 | 10275 | 1.46 | 25 |
| 1310.625 | 32 | 33 | 0.033496 | 8381 | 13585 | 0.62 | 26 |
| 3215.618 | 30 | 28 | 0.034323 | 20032 | 10435 | 1.92 | 27 |
| 1276.530 | 34 | 30 | 0.037827 | 18636 | 11272 | 1.65 | 28 |
| 1147.739 | 60 | 31 | 0.038286 | 10695 | 6897 | 1.55 | 29 |
| 1534.689 | 33 | 33 | 0.039585 | 23402 | 15736 | 1.49 | 30 |
| 2265.983 | 23 | 31 | 0.040197 | 9547 | 4934 | 1.93 | 31 |
| 1415.691 | 37 | 30 | 0.041050 | 12490 | 7111 | 1.76 | 32 |
| 793.557 | 16 | 33 | 0.043446 | 7849 | 5970 | 1.31 | 33 |
| 1363.482 | 34 | 31 | 0.043627 | 17170 | 11572 | 1.48 | 34 |
| 977.476 | 29 | 30 | 0.043710 | 49410 | 22740 | 2.17 | 35 |
| 1128.476 | 34 | 33 | 0.045240 | 15648 | 23901 | 0.65 | 36 |
| 1563.914 | 38 | 34 | 0.045355 | 5838 | 9114 | 0.64 | 37 |
| 1399.623 | 35 | 34 | 0.045650 | 102327 | 54021 | 1.89 | 38 |
| 1242.471 | 38 | 28 | 0.045902 | 7936 | 5019 | 1.58 | 39 |
| 2249.981 | 23 | 33 | 0.046533 | 34037 | 19870 | 1.71 | 40 |

TABLE 5

Peptides Identified as Differentially Abundant in Bound Serum Peptidome (FX2).

| Peptide Mass to Charge Ratio (m/z) | Chromatographic (C18 Reversed Phase) Retention Time (min) | Observation Frequency | Ttest | Mean abundance (Good Responder) | Mean abundance (Poor Responder) | Fold Abundance for [Good]/[Poor] | Rank |
|---|---|---|---|---|---|---|---|
| 1488.818 | 42 | 34 | 0.000001 | 147823 | 50757 | 2.91 | 1 |
| 1117.625 | 25 | 32 | 0.000007 | 6133 | 22243 | 0.28 | 2 |
| 1668.902 | 40 | 34 | 0.000024 | 12583 | 3975 | 3.17 | 3 |
| 986.436 | 31 | 32 | 0.000122 | 7253 | 27593 | 0.26 | 4 |
| 1052.630 | 39 | 34 | 0.000125 | 53490 | 31517 | 1.70 | 5 |

TABLE 5-continued

Peptides Identified as Differentially Abundant in Bound Serum Peptidome (FX2).

| Peptide Mass to Charge Ratio (m/z) | Chromatographic (C18 Reversed Phase) Retention Time (min) | Observation Frequency | Ttest | Mean abundance (Good Responder) | Mean abundance (Poor Responder) | Fold Abundance for [Good]/[Poor] | Rank |
|---|---|---|---|---|---|---|---|
| 1460.631 | 31 | 33 | 0.000245 | 15878 | 95205 | 0.17 | 6 |
| 1896.805 | 33 | 32 | 0.000656 | 13706 | 5861 | 2.34 | 7 |
| 1015.591 | 22 | 31 | 0.000742 | 9538 | 19679 | 0.48 | 8 |
| 801.386 | 24 | 30 | 0.000923 | 4468 | 12803 | 0.35 | 9 |
| 2085.103 | 35 | 28 | 0.001303 | 4989 | 2451 | 2.04 | 10 |
| 1143.653 | 25 | 28 | 0.001558 | 4348 | 12782 | 0.34 | 11 |
| 1653.867 | 38 | 29 | 0.001888 | 5772 | 3520 | 1.64 | 12 |
| 833.271 | 35 | 34 | 0.001980 | 92371 | 52666 | 1.75 | 13 |
| 752.374 | 33 | 34 | 0.003486 | 181889 | 105978 | 1.72 | 14 |
| 1575.838 | 40 | 32 | 0.003892 | 4826 | 2666 | 1.81 | 15 |
| 1812.849 | 29 | 34 | 0.005015 | 10765 | 6936 | 1.55 | 16 |
| 898.422 | 28 | 33 | 0.005278 | 27041 | 15130 | 1.79 | 17 |
| 1476.627 | 31 | 30 | 0.005857 | 2768 | 6520 | 0.42 | 18 |
| 921.519 | 33 | 34 | 0.006905 | 46102 | 33727 | 1.37 | 19 |
| 909.298 | 35 | 34 | 0.007156 | 74842 | 53934 | 1.39 | 20 |
| 831.270 | 35 | 34 | 0.009120 | 143725 | 91221 | 1.58 | 21 |
| 1385.601 | 31 | 30 | 0.009217 | 3924 | 10480 | 0.37 | 22 |
| 1435.731 | 30 | 33 | 0.009711 | 8573 | 5446 | 1.57 | 23 |
| 1377.789 | 40 | 31 | 0.011505 | 6101 | 3161 | 1.93 | 24 |
| 2378.220 | 40 | 33 | 0.014566 | 10901 | 5014 | 2.17 | 25 |
| 1210.582 | 28 | 34 | 0.015581 | 80413 | 47905 | 1.68 | 26 |
| 1401.705 | 31 | 28 | 0.015734 | 6300 | 4004 | 1.57 | 27 |
| 960.475 | 42 | 33 | 0.017667 | 27006 | 13464 | 2.01 | 28 |
| 850.438 | 28 | 33 | 0.018992 | 99230 | 46253 | 2.15 | 29 |
| 1510.791 | 42 | 29 | 0.019051 | 5149 | 2726 | 1.89 | 30 |
| 1489.865 | 38 | 29 | 0.019178 | 4522 | 2586 | 1.75 | 31 |
| 1364.628 | 34 | 31 | 0.023863 | 5368 | 3905 | 1.37 | 32 |
| 1023.640 | 50 | 29 | 0.024563 | 10988 | 4121 | 2.67 | 33 |
| 954.542 | 25 | 30 | 0.025792 | 13945 | 7730 | 1.80 | 34 |
| 829.268 | 37 | 28 | 0.026432 | 73762 | 46511 | 1.59 | 35 |
| 1129.473 | 35 | 33 | 0.026785 | 15128 | 9526 | 1.59 | 36 |
| 2092.117 | 35 | 28 | 0.028361 | 11369 | 5541 | 2.05 | 37 |
| 1078.087 | 20 | 28 | 0.029207 | 6275 | 4129 | 1.52 | 38 |
| 1141.652 | 35 | 32 | 0.029435 | 25135 | 19459 | 1.29 | 39 |
| 892.429 | 36 | 32 | 0.034460 | 34071 | 21526 | 1.58 | 40 |
| 1112.553 | 33 | 29 | 0.037514 | 10049 | 5181 | 1.94 | 41 |
| 847.248 | 36 | 30 | 0.040127 | 52275 | 29856 | 1.75 | 42 |
| 1148.510 | 28 | 30 | 0.040211 | 5540 | 10433 | 0.53 | 43 |
| 1504.820 | 40 | 34 | 0.041511 | 30383 | 15588 | 1.95 | 44 |
| 723.197 | 19 | 28 | 0.042047 | 5110 | 3221 | 1.59 | 45 |
| 2051.080 | 38 | 28 | 0.043654 | 2875 | 1920 | 1.50 | 46 |
| 918.550 | 25 | 32 | 0.045376 | 18757 | 12421 | 1.51 | 47 |
| 925.281 | 34 | 32 | 0.047311 | 18635 | 11566 | 1.61 | 48 |
| 1521.775 | 33 | 30 | 0.047430 | 6822 | 16717 | 0.41 | 49 |
| 1326.630 | 29 | 28 | 0.047724 | 3003 | 5721 | 0.52 | 50 |
| 1312.680 | 22 | 29 | 0.049059 | 4013 | 2748 | 1.46 | 51 |

Example 3

Identification of Peptide Amino Acid Sequences

Using the software programs Matrix Science Mascot and Protein Pilot Paragon, amino acid sequences were tentatively assigned to a total of 17 peptides (Table 1) corresponding to six parent proteins. These peptide fragments were derived from a fibronectin III domain of Oncostatin M receptor beta chain (OSMRβ), fibrinogen alpha chain (FGA), fibrinogen/fibrinopeptide B (FGB), a fragment of the signal peptide region of the cysteine and histidine-rich protein 1 (CYHR1), coagulation factor XIII chain A (F13A) and Complement C3 (CO3). One peptide (1534.689 m/z) was assigned slightly different but overlapping amino acid sequences by the Mascot and the Paragon algorithms. Seven peptide masses required post-translational modifications to explain MS/MS fragmentation spectra. Four peptides were N-terminally modified including two FGA modifications that were assigned a mass value only. One FGA modification was assigned as a post-translationally hydroxylated phenylalanine given that the F27Y polymorphism has not been reported. One FGB peptide was assigned with an N-terminal gyro-glutamate residue resulting from an N-terminal glutamine rearrangement. Two OSMR peptides were assigned mass values consistent with modifications including disodiation (+45.99 m/z) and O-glucosamine (O-GlcN) modification Example 4

Differential Expression of Intact OSMRβ and CYHR1 in Patient Serum

Figure 4A:
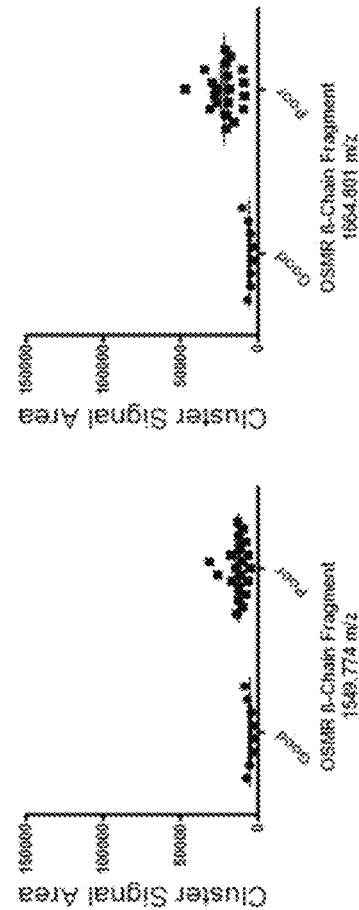
FIGS. 4A-4E are graphs (FIGS. 4A-4D) and an image of an immunoblot (FIG. 4E) showing the distribution of serum oncostatin M receptor β chain (OSMRβ) fragments and protein levels associated with erythropoietic agent responsiveness, where peptide abundance data was extracted from aligned mass spectrometry data sets and peptide spectral abundance was calculated from the MS ion cluster area (10), and where vertical scatter plots (mean±SEM) for the differences in serum abundance for three OSMRβ fragments (FIGS. 4A-4C) and for densitometry measurements of circulating OSMRβ (FIGS. 4C-4D) illustrate significant differences in abundance between good responder and poor responder groups.
Figure 4B:
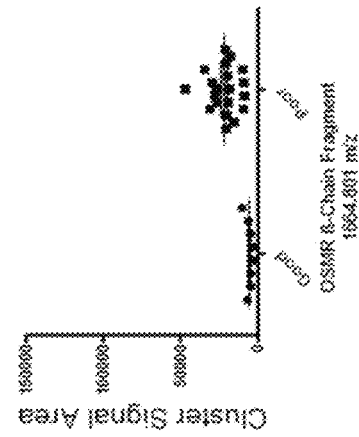
Figure 4C:
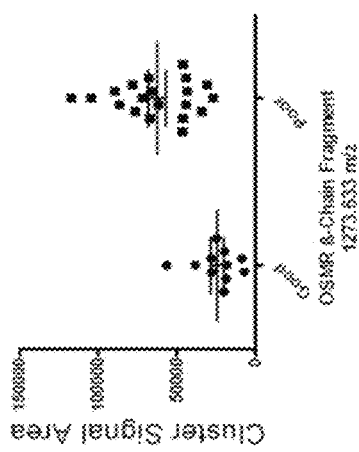
Figure 4D:
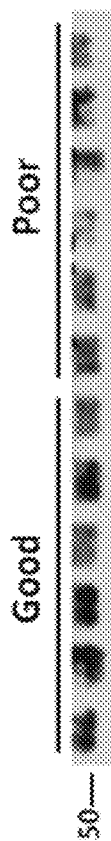
Figure 4E:
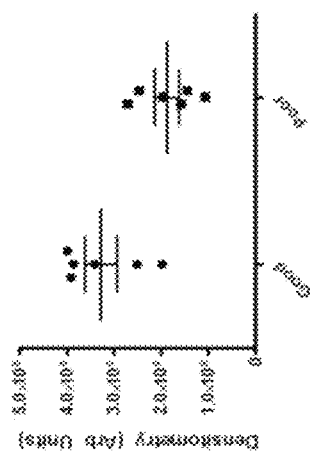

Immunoblotting experiments were performed to determine if the intact OSMRβ and CYHR1 proteins in serum correlated with the differential peptide expressions that were observed. In reducing and denaturing conditions, an OSMR positive band was identified migrating at 50 kDa (FIGS. 4D-E) and was significantly ($p<0.05$) increased (75% above poor responders) in the serum of good responders. The analysis of these samples using non-reducing and denaturing SDS-PAGE gels identified OSMR bands migrating at 100-110 kDa with a like expression trend. Similarly, CHYR1 was identified (FIG. 5C) and validated using immunogen peptide blocking experiments (FIG. 5D) migrating at approximately 72 kDa and was significantly (FIG. 5B; p<0.05) increased in the serum of EPO hypo-responders (30% above good responders).

Example 5

Statistical Analysis of Identified Peptides

Summary statistics for all identified peptides are shown in Table 6. In the case of OSMRβ and FGA, more than one fragment of a parent protein was identified and a Bonferroni adjusted p-value is shown and an analysis of the sum of the fragment abundances was performed. In addition, the ROC value associated with the sensitivity and specificity of the peptide to predict either good or poor response was calculated.

ined. To that end, an immunoblot analysis of the serum for the presence of OSMRβ (reducing and non-reducing conditions) and CYHR1 (reducing conditions) was performed in a subset of the total population. The results of the OSMRβ immunoblot experiments suggested that the receptor is present in the serum as a dimer. The molecular weight of the receptor observed in reducing conditions was consistent with molecular weights for shed OSMR, LIF, and IL-6R ecto-domains (11, 12). The presence of both intact proteins in serum was also demonstrated, with OSMR increased in the serum of good responders and CYHR1 increased in the serum of poor responders.

In comparing the abundance of intact protein by immunoblot to peptide fragments from LCMS, different patterns were observed. For OSMR, intact protein was high in the serum of good responders while peptide fragments were high in poor responders. For CYHR1, intact protein was high in the serum of poor responders while peptide fragments were high in the serum of good responders. Without wishing to be bound by any particular theory, it was thought that the difference was due to altered catabolism of OSMR

TABLE 6

Statistical Analysis of the Identified Peptides.

| Peptide | m/z | Group | Gender (p values+) | Interaction | ROC* |
| --- | --- | --- | --- | --- | --- |
| OSMR | 1273 | <0.0001 (<0.0001) | 0.040 (1.00) | 0.85 (1.00) | 0.95 |
|  | 1549 | <0.0001 (<0.0001) | 0.026 (0.08) | 0.21 (0.63) | 0.96 |
|  | 1664 | <0.0001 (<0.0001) | 0.19 (0.56) | 0.62 (1.00) | 0.99 |
| Sum of Fragments |  | <0.0001 | 0.20 | 0.65 | 0.98 |
| CYHR1 | 1488 | <0.0001 | 0.60 | 0.60 | 0.089 |
| FGA | 1194 | 0.052 (0.47) | 0.49 (1.00) | 0.29 (1.00) | 0.21 |
|  | 1399 | 0.081 (0.73) | 0.67 (1.00) | 0.92 (1.00) | 0.38 |
|  | 1463 | 0.021 (0.19) | 0.58 (1.00) | 0.33 (1.00) | 0.31 |
|  | 1481 | 0.045 (0.041) | 0.46 (1.00) | 0.80 (1.00) | 0.28 |
|  | 1534 | 0.063 (0.57) | 0.78 (1.00) | 0.85 (1.00) | 0.38 |
|  | 2466 | 0.03 (0.27) | 0.067 (0.60) | 0.85 (1.00) | 0.18 |
|  | 2553 | 0.019 (0.17) | 0.27 (1.00) | 0.59 (1.00) | 0.19 |
|  | 2768 | 0.053 (0.48) | 0.16 (1.00) | 0.58 (1.00) | 0.23 |
|  | 2931 | 0.004 (0.036) | 0.17 (1.00) | 0.33 (1.00) | 0.19 |
| Sum of Fragments |  | 0.005 | 0.17 | 0.59 | 0.12 |
| FGB | 1552 | 0.0010 | 0.89 | 0.72 | 0.20 |
| Factor XIII | 1210 | 0.015 | 0.51 | 0.71 | 0.25 |
| Complement C3 | 1504 | 0.07 | 0.64 | 0.20 | 0.26 |

*values for ROC are the area under the curve with values greater than 0.5 predictive of poor response and values less than 0.5 predictive of good response
+p values follow Bonferroni correction for multiple comparisons Discussion of Examples 1-5

One of the goals of the study was to identify serum peptides associated specifically with a poor response to EPO. To that end, patients that routinely attended their dialysis session, received adequate EPO and iron dosing, and did not appear to have risk factors for erythropoietin failure, such as chronic inflammation or infection, were studied. Using a peptidomic approach to generate MS data and develop a list of differentially abundant peptides and ranked on p-values, amino acid sequences were assigned to 16 peptides whose serum abundance significantly differed between poor and good responders for further analysis. Three of the serum peptides associated with poor EPO response, through sequence alignment of the peptides to the parent protein, were found to be derived from the fibronectin III domain of the OSMRβ chain. The 13 serum peptides associated with good EPO response were observed to be derived from FGA, FGB, FXIIIA, CO3, and CYHR1.

Whether the serum peptide fragment differences reflected changes in the intact protein in the serum was also examand CYHR1 over the range of ERI or increased receptor turnover in the case of OSMR. Animal data appear to support this speculation for OSMR, where OSMR knockout mice have low hematocrit and decreased RBC's (13).

These findings were not confounded with other measured markers of EPO response. Differences between poor and good responders were not observed for C-reactive protein, hepcidin, IL-6, IL-7, IL-8, IL-10, TNF-α, transferrin saturation (Tsat), ferritin, and albumin. There was a significant interaction between responder type and gender for hepcidin, IL-6 and IL-8. It was thought that the gender interaction is most likely related to several male poor responders that showed signs of inflammation in their measured laboratory values.

Three fragments of OSMRβ were found to be strongly associated with a poor EPO response and one fragment of CYHR1 was found to be strongly associated with a good EPO response. Oncostatin-M (OSM) is proposed to be an important EpoR-phosphoY343-Stat5 induced gene product that participates in erythroblast survival (14). OSM is secreted from cytokine activated T cells and monocytes and is involved in inflammation (15,16). OSM binds to two different OSM receptors in humans: the type 1 receptor is identical to leukemia inhibitory factor (LIF) receptor that consists of gp130, also found in the IL-6 receptor; and, the type 2 receptor which consists of gp130 and OSM-specific receptor β subunit (OSMR) (17,18). The OSMR fragments identified in the serum of the present patients were from the type 2 receptor.

Animal studies indicate that OSMR may play an important role in erythropoiesis as OSMR knockout mice have a decreased number of circulating RBC and a decreased hematocrit compared to wild type (13). OSMR knockout mice also have decreased numbers of erythroid colony forming units and erythrocyte-producing colonies in the bone marrow. Work in human fibroblast or epithelial cells show that OSM ligand binding to OSMR induces receptor degradation and then increases the level of receptor synthesis (19). In hepatocytes and hepatoma cells, OSM induces hypoxia-inducible factor 1α gene transcription via a Janus kinase/signal transducer (20).

Analysis of the estimated amino acid sequence of the fragment of CYHR1 showed that the peptide was enriched in hydrophobic amino acids and derived from the signal peptide sequence of CYHR1. This enrichment of hydrophobic amino acids was consistent with the peptide being recovered from the serum interactome fraction (the protein bound serum peptide fraction). This CYHR1 fragment was a similar predictor of a good response (ROC=0.91) as OSMR was observed to be a predictor of a poor response (ROC=0.98).

The current state of knowledge on CYHR1 is limited to its predicted protein structure, protein-protein interactions, subcellular localization and chromosome mapping. CYHR1 is proposed to contain four functional transmembrane helices and was first identified using a yeast two-hybrid system to search for cytoplasmic proteins that associate with galectin-3 (21). Subcellular localization of CYHR1 in 3T3 cells by confocal microscopy showed concentrations at the nuclear envelope and cytoplasm, but not in the nucleus. It was not clear from the published data if the cytoplasmic pool is resident in a unique organellar membrane fraction or truly cytoplasmic. Further work was performed using recombinant hamster galectin-3 and murine CYHR1 and demonstrated that CYHR1 binds to the carbohydrate-recognition domain of galectin-3 (22).

Other peptides were also identified in the serum of these subjects that had increased abundances in good responders. These peptides were attributed to FGA, FGB, F XIIIA, and CO3 and may be related to low levels of inflammation that are present in hemodialysis patients (23). The prediction of EPO response has been related to the baseline fibrinogen, baseline transferrin receptor concentration and the change in the transferrin receptor concentration after 2 weeks for EPO therapy (3). The observed increase in abundance of fragments of both fibrinogen and factor XIII maybe related through thrombin and a result of inflammation (24). In a study of 100 hemodialysis patients in which many proposed markers of inflammation were measured, the authors concluded that subclinical inflammation was an important determinant of anemia (25). Further, the authors of this manuscript were able to look at 51 subjects that had not received EPO and found that there was a negative relationship between Hb and fibrinogen in ESA treated subjects but not in non-ESA treated subjects.

In summary, a peptidomic analysis was performed on the serum of subjects without overt signs of inflammation or extraordinary blood loss that were good- and poor-responders to exogenous EPO. The analysis resulted in the identification of 16 peptide fragments that were differentially expressed in the two groups, with OSMRβ and CYHR1 showing a good association. The other identified fragments, fibrinogen α and β, factor XIII, and compliment C3, were not as strongly associated with ESA response and may reflect an underlying inflammatory process.

Throughout this document, various references are mentioned. All such references are incorporated herein by reference, including the references set forth in the following list:

REFERENCES

1. Zhang, Y., Thamer, M., Stefanik, K., Kaufman, J., Cotter, D. J. 2004. Epoetin requirement predict mortality in hemodialysis patients. Am. J. Kidney Dis. 44:866-876.
2. Szczech. L. A., Barnhart, H. X., Inrig, J. K., Reddan, D. N., Sapp, S., Califf, R. M., Patel, U. D., Singh, A. K. 2008. Secondary analysis of the CHOIR trial epoetin-α dose and achieved hemoglobin outcomes. Kidney Int. 74:791-798.
3. Danielson, B. 1995. R-HuEPO hyporesponsiveness—who and why? Nephrol. Dial. Transplant. 10:69-73.
4. Goicoechea, M., Martin, J., de Sequera, P., Quiroga, J. A. Ortiz, A., Carreño, V., Caramelo, C. 1998. Role of cytokines in the response to erythropoietin in hemodialysis patients. Kidney Int. 54:1337-1343.
5. Van der Putten, K., Braam, B., Jie, K. E., Gaillard, C. A. J. M. 2008. Mechanisms of disease: erythropoietin resistance in patients with both heart and kidney failure. Nat. Clin. Pract. Nephrol. 4:47-57.
6. Nemeth, E., Rivera, S., Gabayan, V., Keller, C., Taudorf, S., Pedersen, B. K., Ganz, T. 2004. IL-6 mediates hypoferremia of inflammation by inducing the synthesis of the iron regulatory hormone hepcidin. J. Clin. Invest. 113:1271-1276.
7. Andrews, N.C. 2004. Anemia of inflammation: the cytokine-hepcidin link. J. Clin. Invest. 113:1251-1253
8. Khankin, E. V. Mutter, W. P., Tamez, H., Yuan, H. T. Karumanchi, S. A., Thadhani, R. 2010. Soluble erythropoietin receptor contributes to erythropoietin resistance in end-stage renal disease. PLoS One. 16:e9246.
9. Inrig, J. K., Patel, U., Bryskin, S., Szczech, L. 2009. Association between high-dose ESA, inflammatory biomarkers, and soluble erythropoietin receptors. J. Am. Soc. Nephrol. 20:143A.
10. Mann, M. and Kelleher, N. L. 2008. Precision proteomics: The case for high resolution and high mass accuracy. Proc. Nat. Acad. Sci. 105:18132-18138
11. Matthews V., Schuster B., Schütze S., Bussmeyer I., Ludwig A., Hundhausen C., Sadowski T., Saftig P., Hartmann D., Kallen K. J., Rose-John S. 2003. Cellular cholesterol depletion triggers shedding of the human interleukin-6 receptor by ADAM10 and ADAM17 (TACE). J Biol Chem. 278:38829-39
12. Chen D, Chu C Y, Chen C Y, Yang H C, Chiang Y Y, Lin T Y, Chiang I P, Chuang D Y, Yu C C, Chow K C. 2008 Expression of short-form oncostatin M receptor as a decoy receptor in lung adenocarcinomas. J Pathol. 215:290-9
13. Tanka, M., Hirgayashi, Y., Sekiguchi, T., Inoue, T., Katsuki, M., Miyajima, A. 2003. Targeted disruption of oncostatin M receptor results in altered hematopoiesis. Blood. 102:3154-3162.
14. Menon, M. P., Karur, V., Bogacheva, O., Cuetarea, B., Wojchowski, D. M. 2006. Signals for stress erythropoiesis are integrated via and erythropoietin receptor-phosphotyrosine-343-Stat5 axis. J. Clin. Invest. 116:683-694.
15. Brown, T. J., Lioubin, M. N., Marquardt, H. 1987. Purification and characterization of cytostatic lymphokines produced by activated human T lymphocytes: synergistic antoproliferative activity of transforming growth factor beta 1, interferon-gamma, and oncostatin M for human melanoma cells. J. Immunol. 139:2977-2983.
16. Malik, N., Kallestad, J. C., Gunderson, N. L., Austin, S. D., Neubauer, M. G., Ochs, V., Marquardt, H., Zarling, J. M., Shoyab, M., Wei, C. M., et al. 1989. Molecular cloning, sequence analysis, and functional expression of a novel growth regulator, oncostatin M. Mol. Cell Biol. 9:2847-2853.
17. Thoma B, Bird T A, Friend D J, Gearing D P, Dower S K. 1994. Oncostatin M and leukemia inhibitory factor trigger overlapping and different signals through partially shared receptor complexes. J Biol Chem. 269:6215-22.
18. Mosley B, De Imus C, Friend D, Boiani N, Thoma B, Park L S, Cosman D. 1996. Dual oncostatin M (OSM) receptors. Cloning and characterization of an alternative signaling subunit conferring OSM-specific receptor activation. J Biol Chem. 271:32635-32643.
19. Blanchard, F., Wang, Y., Kinzie, E., Durlomb, L., Godard, A., Baumann, H. 2001. Oncostatin M regulates the synthesis and turnover of gp130, leukemia inhibitory factor receptor α, and oncostatin M receptor β by distinct mechanisms. J. Biol. Chem. 50:47038-47045.
20. Vollner, S., Kappler V., Kaczor, J., Flügel, D., Rolvering, C., Kato, N., Kietzman, T., Behrmann, I., Haan, C. 2009. Hypoxia-inducible factor 1α is up-regulated by oncostatin M and participates in oncostatin M signaling. Hepatology 50:253-260.
21. Menon, R. P., Strom, M., Hughes, R. C. 2000. Interaction of a novel cysteine and histidine-rich cytoplasmic protein with galectin-3 in a carbohydrate-independent manner. FEBS Lett. 470:227-231.
22. Bawumia, S. Barboni, E. A. M., Menon, R. P., Hughes, R. C. 2003. Specificity of interactions of galectin-3 with Chrp a cysteine- and histidine-rich cytoplasmic protein. Biochimie 85:189-194.
23. Kaysen G. A. 2001. The microinflammatory state in uremia: causes and potential consequences. J. AM. Soc. Nephrol. 12:1549-1557.
24. Narayanan, S. 1999. Multifunctional roles of thrombin. Ann. Clin. Lab. Sci. 29:275-280.
25. Borawski, J., Pawlak, K., Myśliwiec, M. 2002. Inflammatory markers and platelet aggregation tests as predictors of hemoglobin and endogenous erythropoietin levels in hemodialysis patients. Nephron. 91:671-681.
26. Merchant, M. L., Perkins, B. A., Boratyn, G. M., Ficociello, L. H., Wilkey, D. W., Barati, M. T., Bertram, C. C., Page, G. P., Rovin, B. H., Warram, J. H., et al. 2009. Urinary peptidome may predict renal function decline in type 1 diabetes and microalbuminuria. *J Am Soc Nephrol* 20:2065-2074.
27. Merchant, M. L., Cummins, T. D., Wilkey, D. W., Salyer, S. A., et al., 2008. Proteomic analysis of renal calculi indicates an important role for inflammatory processes in calcium stone formation. *Am J Physiol Renal Physiol* 295, F1254-1258.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for predicting a response to an erythropoietic agent in a subject, comprising:

(a) providing a biological sample from a subject who has been previously administered a dose amount of an erythropoietic agent;

(b) measuring an amount in the sample of the peptide consisting of SEQ ID NO: 15;

(c) comparing the amount of the peptide in the sample to a control level of the peptide;

(d) predicting that the subject will have a poor response to the erythropoietic agent when there is a measurable increase in the amount of the peptide consisting of SEQ ID NO: 15 in the sample as compared to the control level; and (e) modifying the dose amount of the erythropoietic agent being administered to the subject by administering an increased dose amount of the erythropoietic agent to the subject predicted to have a poor response to the erythropoietic agent in (d), wherein the increased dose amount of the erythropoietic agent is increased as compared to the dose amount of the erythropoietic agent previously administered to the subject.

2. The method of claim 1, further comprising applying the biological sample to a device capable of affecting detection of the peptide.

3. The method of claim 1, wherein the subject has kidney disease, anemia, or cancer.

4. The method of claim 1, wherein the biological sample comprises blood, plasma, serum, or urine.

5. The method of claim 1, wherein the subject is human.

6. The method of claim 1, wherein measuring the amount in the sample of the peptide is performed using mass spectrometry (MS) analysis, immunoassay analysis, or both.

7. The method of claim 6, wherein the immunoassay analysis comprises an enzyme-linked immunosorbent assay (ELISA).

8. A method for determining whether to modify an amount of an erythropoietic agent administered to a subject, comprising:

(a) providing a series of biological samples over a time period from a subject who has been previously administered a dose amount of an erythropoietic agent;

(b) analyzing the series of biological samples to measure an amount of the peptide consisting of SEQ ID NO: 15 in each of the biological samples;

(c) comparing any measurable change in amounts of the peptide in each of the biological samples over the time period;

(d) identifying the subject as being in need of an administration of an increased amount of the erythropoietic agent if there is a measurable increase in the amount of the peptide over the time period; and (e) modifying the amount of the erythropoietic agent being administered to the subject by administering an increased dose amount of the erythropoietic agent to the subject identified as being in need in (d), wherein the increased dose amount of the erythropoietic agent is increased as compared to the dose amount of the erythropoietic agent previously administered to the subject.

9. The method of claim 8, wherein the subject has kidney disease, anemia, or cancer.

10. The method of claim 8, wherein the biological samples comprise blood, plasma, serum, or urine.

11. The method of claim 8, wherein the subject is human.

12. The method of claim 8, wherein measuring the amount of the peptide in each of the biological samples is performed using mass spectrometry (MS) analysis, immunoassay analysis, or both.

13. The method of claim 12, wherein the immunoassay analysis comprises an enzyme-linked immunosorbent assay (ELISA).

* * * * *